(12) United States Patent
Bansal

(10) Patent No.: US 9,243,060 B2
(45) Date of Patent: Jan. 26, 2016

(54) HUMANIZED ANTI-FACTOR C3B ANTIBODIES AND USES THEREOF

(71) Applicant: NovelMed Therapeutics, Inc., Cleveland, OH (US)

(72) Inventor: Rekha Bansal, Twinsburg, OH (US)

(73) Assignee: Novelmed Therapeutics, Inc., Cleveland, OH (US)

( * ) Notice: Subject to any disclaimer, the term of this patent is extended or adjusted under 35 U.S.C. 154(b) by 0 days.

(21) Appl. No.: 14/390,645

(22) PCT Filed: Apr. 2, 2013

(86) PCT No.: PCT/US2013/034990
§ 371 (c)(1),
(2) Date: Oct. 3, 2014

(87) PCT Pub. No.: WO2013/152024
PCT Pub. Date: Oct. 10, 2013

(65) Prior Publication Data
US 2015/0064202 A1    Mar. 5, 2015

Related U.S. Application Data

(60) Provisional application No. 61/619,860, filed on Apr. 3, 2012.

(51) Int. Cl.
*A61K 39/395* (2006.01)
*C07K 16/36* (2006.01)
*C07K 16/18* (2006.01)

(52) U.S. Cl.
CPC ............. *C07K 16/18* (2013.01); *C07K 2317/21* (2013.01); *C07K 2317/24* (2013.01); *C07K 2317/54* (2013.01); *C07K 2317/55* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 2003/0198636 A1 | 10/2003 | Gupta-Bansal |
| 2008/0317746 A1 | 12/2008 | Bauerle et al. |
| 2010/0111946 A1 | 5/2010 | Bansal |
| 2010/0291106 A1 | 11/2010 | Etemad-Gilbertson |

FOREIGN PATENT DOCUMENTS

WO    9742317 A1    11/1997

OTHER PUBLICATIONS

Colman, Research in Immunology 145: 33-36, 1994.*
Kussie et al., J. Immunol. 152: 146-152, 1994.*
Chen et al., EMBO J., 14: 2784-2794, 1995.*
Rudikoff et al., Proc Natl Acad Sci USA 79: 1979-1983 ,1982.*

* cited by examiner

*Primary Examiner* — Phillip Gambel
(74) *Attorney, Agent, or Firm* — Tarolli, Sundheim, Covell & Tummino LLP

(57) ABSTRACT

A method of inhibiting complement activation mediated by C3b inhibitors in a subject includes administering a C3b inhibitor to the subject to inhibit at least one of C3b binding to factors B and properdin, inhibit C3 cleavage, inhibit the activation of neutrophils, monocytes, platelets, and endothelium; or inhibit the formation of C3a, C5a, and MAC.

15 Claims, 22 Drawing Sheets

Amino Acid Sequence of the Murine Anti-C3b Antibody
CDRs are in Red

ANTI-C3B – MURINE - HC

QVQLQQSGAEIVKPGASVKMSCKASGYTFTSYWINWVKQRPGQGLEWIGDIYPVRGITNYSEKFKNKAKMIPDTSSSTVY
MQLSSLTSEDSAVYYCSRGNFGNFDAMDYWGQGTSVTVSSAKTT

ANTI-C3B – MURINE - LC

QIVLTQSPAILSASPGEKVTMTCSATSSITYIHWYQQKSGTSPKRWIYDTSRLASGVPTRFSGSGSGTSYSLTISTMEAEDA
ATYYCQQWSSNPPTFGGGTKLEIKRTVA

Fig. 17

Amino Acid Sequence of Murine and Humanized Anti-C3b Antibody

>Anti–C3b – MURINE CLONE 7D11 – HC, SEQ ID NO 1:
QVQLQQSGAEIVKPGASVKMSCKASGYTFTSYWINWVKQRPGQGLEWIGDIYPVRGITNYSEKFKNKAKMIPDTSSSTVYMQLSSLTSEDSAVYYCSRGNFGNFDAMDYWGQGTSVTVSS >Anti–C3b – MURINE CLONE 7D11 – LC, SEQ ID NO 2:
QIVLTQSPAILSASPGEKVTMTCSATSSITYIHWYQQKSGTSPKRWIYDTSRLASGVPTRFSGSGSGTSYSLTISTMEAEDAATYYCQQWSSNPPTFGGGTKLEIKRTVA >Anti–C3b – HUMANIZED CLONE W – HC, SEQ ID NO 3:
EVQLVQSGAEVKKPGESLRISCKGSGYTFTSYWINWIRQSPSRGLEWLGDIYPVRGITNYSEKFKNRVTISADKSTAYLQWSSLKASDTAMYYCARGNFGNFDAMDYWGQGTLVTVSS >Anti–C3b – HUMANIZED CLONE W – LC, SEQ ID NO 4:
DIQMTQSPSSLSASVGDRVTITCSATSSITYIHWYQCKPGKAPKLLIYDTSRLASGVPSRFSGSGSGTEFTLTISSLQSEDFAVYYCQQWSSNPPTFGQGTKVEIKRTVA >Anti–C3b – HUMANIZED CLONE X – HC, SEQ ID NO 5:
EVQLVESGGGLVQPGRSLRLSCAASGYTFTSYWINWVRQAPGKGLEWVSDIYPVRGITNYSEKFKNRFTISRDNAKNSLYLQMNSLRAEDTAVYYCAKGNFGNFDAMDYWGQGTLVTVSS >Anti–C3b – HUMANIZED CLONE X – LC, SEQ ID NO 6:
DIQMTQSPSSLSASVGDRVTITCSATSSITYIHWYQQKPGKAPKLLIYDTSRLASGVPSRFSGSGSGTDFTLTISSLQPEDVATYYCQQWSSNPPTFGQGTKVEIKRTVA >Anti–C3b – HUMANIZED CLONE Y – HC, SEQ ID NO 7:
EVQLVESGGGLVQPGGSLRLSCAASGYTFTSYWINWVRQAPSKGLEWVGDIYPVRGITNYSEKFKNRFTFSLDTSKSTAYLQMNSLRAEDTAVYYCAKGNFGNFDAMDYWGQGTLVTVSS >Anti–C3b – HUMANIZED CLONE Y – LC, SEQ ID NO 8:
DIQMTQSPSSLSASVGDRVTITCSATSSITYIHWYQQKPGKAPKVLLIYDTSRLASGVPSRFSGSGSGTDFTLTISSLQPEDFATYYCQQWSSNPPTFGQGTKVEIKRTVA >Anti–C3b – HUMANIZED CLONE Z – HC, SEQ ID NO 9:
QVQLQESGPGLVKPSQTLSLTCTVSGYTFTSYWINWVRQATGQGLEWMGDIYPVRGITNYSEKFKNRVTITADKSTSTAYMELSSLRSEDTAVYYCARGNFGNFDAMDYWGQGTLVTVSS >Anti–C3b – HUMANIZED CLONE Z – LC, SEQ ID NO 10:
DIQMTQSPSSLSASVGDRVTITCSATSSITYIHWYQQKPGKAPKLLIYDTSRLASGIPPRFSGSGVGTEFTFTISSLEAEDAATYYCQQWSSNPPTFGQGTKVEIKRTVA

Fig. 18

Amino Acid Sequence of the CDRs and Framework Regions

Anti – C3b – HUMANIZED CLONE W

Anti – C3b – HUMANIZED CLONE W- HC

| | |
|---|---|
| SEQ ID NO 11 | EVQLVQSGAEVKKPGESLRISCKGS |
| SEQ ID NO 12 | GYTFTSYWIN |
| SEQ ID NO 13 | WIRQSPSRGLEWLG |
| SEQ ID NO 14 | DIYPVRGITNYSEKFKN |
| SEQ ID NO 15 | RVTISADKSISTAYLQWSSLKASDTAMYYCAR |
| SEQ ID NO 16 | GNFGNFDAMDY |
| SEQ ID NO 17 | WGQGTLVTVSS |

Anti – C3b – HUMANIZED CLONE W- LC

| | |
|---|---|
| SEQ ID NO 18 | DIQMTQSPSSLSASVGDRVTITC |
| SEQ ID NO 19 | SATSSITYIH |
| SEQ ID NO 20 | WYQQKPGKAPKLLIY |
| SEQ ID NO 21 | DTSRLAS |
| SEQ ID NO 22 | GVPSRFSGSGSGTEFTLTISSLQSEDFAVYYC |
| SEQ ID NO 23 | QQWSSNPPT |
| SEQ ID NO 24 | FGQGTKVEIKRTVA |

Fig. 19

Amino Acid Sequence of the Framework Regions

Anti – C3b – CLONE X

Anti – C3b – CLONE X - HC
| | |
|---|---|
| SEQ ID NO 25 | EVQLVESGGGLVQPGRSLRLSCAAS |
| SEQ ID NO 26 | WVRQAPGKGLEWVS |
| SEQ ID NO 27 | RFTISRDNAKNSLYLQMNSLRAEDTAVYYCAK |
| SEQ ID NO 28 | WGQGTLVTVSS |

Anti – C3b – CLONE X - LC
| | |
|---|---|
| SEQ ID NO 29 | DIQMTQSPSSLSASVGDRVTITC |
| SEQ ID NO 30 | WYQQKPGKAPKLLIY |
| SEQ ID NO 31 | GVPSRFSGSGSGTDFTLTISSLQPEDVATYYC |
| SEQ ID NO 32 | FGQGTKVEIKRTVA |

Fig. 20

Amino Acid Sequence of the Framework Regions

Anti – C3b – CLONE Y

Anti – C3b – CLONE Y – HC

SEQ ID NO 33   EVQLVESGGGLVQPGGSLRLSCAAS
SEQ ID NO 34   WVRQAPGKGLEWVG
SEQ ID NO 35   RFTFSLDTSKSTAYLQMNSLRAEDTAVYYCAK
SEQ ID NO 36   WGQGTLVTVSS

Anti – C3b – CLONE Y – LC

SEQ ID NO 37   DIQMTQSPSSLSASVGDRVTITC
SEQ ID NO 38   WYQQKPGKAPKVLIY
SEQ ID NO 39   GVPSRFSGSGSGTDFTLTISSLQPEDFATYYC
SEQ ID NO 40   FGQGTKVEIKRTVA

Fig. 21

Amino Acid Sequence of the Framework Regions

Anti – C3b – CLONE Z

Anti – C3b – CLONE Z - HC

| | |
|---|---|
| SEQ ID NO 41 | QVQLQESGPGLVKPSQTLSLTCTVS |
| SEQ ID NO 42 | WVRQATGQGLEWMG |
| SEQ ID NO 43 | RVTITADKSTSTAYMELSSLRSEDTAVYYCAR |
| SEQ ID NO 44 | WGQGTLVTVSS |

Anti – C3b – CLONE Z - LC

| | |
|---|---|
| SEQ ID NO 45 | DIQMTQSPSSLSASVGDRVTITC |
| SEQ ID NO 46 | WYQQKPGKAPKLLIY |
| SEQ ID NO 47 | GIPPRFSGSGYGTEFTFTISSLEAEDAATYYC |
| SEQ ID NO 48 | FGQGTKVEIKRTVA |

HUMANIZED ANTI-FACTOR C3B ANTIBODIES AND USES THEREOF

RELATED APPLICATION

This application claims priority from U.S. Provisional Application Ser. No. 61/619,860, filed Apr. 3, 2012, which claims priority from U.S. patent application Ser. No. 12/532,740, filed Sep. 23, 2009, the subject matter of which are incorporated herein by reference in their entirety.

GOVERNMENT FUNDING

This invention was made with government support under Grant No. R44HL102890 awarded by The National Institutes of Health. The United States government has certain rights to the invention.

TECHNICAL FIELD

The present invention relates to humanized and chimeric antibodies and antigen-binding fragments thereof with complement pathway inhibitory function having reduced effector functions and immunogenicity. The humanized and chimeric monoclonal antibodies of this invention selectively block the binding of factor B to C3b without inhibiting the classical pathway activation. These antibodies do not inhibit the interaction of C3b to C5 and therefore have a unique function in inhibiting the alternative pathway. Such antibodies are useful treatments for disease indications where alternative complement pathway plays a pathological role.

BACKGROUND

The complement system is activated via three distinct pathways; the classical pathway, the lectin pathway and the alternative complement pathway (AP). The classical pathway is activated via antigen-antibody complexes. The lectin pathway is a variation of the classical pathway and the alternative pathway is activated by foreign material, artificial surfaces, dead tissues, bacteria, dead yeast cells.

The classical complement pathway is important for host defense against pathogens. Activation of the classical pathway generates C3a, C4a, C5a and C5b-9 molecules, which activates a variety of cells in response to host defense. In pathological conditions, as a result of activation of the alternative pathway, anaphylatoxins C3a, C5a are formed and tissues damaging C5b-9 molecules, also known as the membrane attack complex (MAC), are formed. These molecules mediate inflammation via cellular activation and release of inflammatory mediators. In addition to its role as a lytic pore-forming complex, there is strong evidence that the depositing of sublytic MAC may play an important role in inflammation.

The alternative complement pathway is activated in pathological inflammation. Elevated levels of C3a, C5a, and C5b-9 have been found associated with multiple acute and chronic disease conditions. These inflammatory molecules activate neutrophils, monocytes and platelets. Therefore, inhibition of disease-induced AP activation is important for clinical benefit in the diseases where complement activation plays a role in disease pathology.

In addition to its essential role in immune defense, the complement system contributes to tissue damage in many clinical conditions. The activities included in the complement biochemical cascade present a potential threat to host tissue. An example includes the indiscriminate release of destructive enzymes possibly causing host cell lysis. Thus, there is a pressing need to develop therapeutically effective complement inhibitors to prevent these adverse effects.

In a disease condition where AP activation contributes to disease pathology, elevated levels of C3a, C5a and C5b-9 molecules are found in serum, plasma, blood or other body fluids representative of the disease. Production and inhibition of each of these molecules via different mechanisms is important for diseases. One possible mechanism for inhibiting the formation of active C3 convertase is via the use of an anti-C3b antibody. Thus blocking/inhibiting or preventing AP activation via depleting C3b, neutralizing C3b, C3c or inactivating C3b remains an important therapeutic strategy.

The application developed humanized and chimeric antibody sequences that are novel and provide targeted binding to C3b. The binding of C3b to B, and not C3b to C5, is inhibited by this antibody. C3a, C5a, and C5b-9 all drive inflammation and also amplify the AP activation process. Anti-C3b agents that bind C3b and prevent B interaction include but not limited to monoclonal and polyclonal antibodies, chimeric, humanized, fully human, and nano-antibodies, Full length and fragments thereof including IgG, Fab, Fab', F(ab')$_2$, and IgGs. Apatamers, small molecules, and SiRNA can also neutralize C3b binding to B and prevent production of AP induced production of C3a, C5a, and C5b-9. As a result, cellular activation, inflammation and release of inflammatory mediators are also prevented. Because AP activation is linked to various acute and chronic human diseases, the blockade with anti-C3b agents will also block the inflammation process providing clinical benefit to mammals treated with the anti-C3b monoclonal antibodies.

Complement is one of several factors involved in pathogenesis and could be a significant pathological mechanism that offers an effective point for clinical control. The need for effective complement inhibitory drugs is signified by growing recognition of the importance of complement-mediated tissue injury in a variety of disease states. Despite this, currently there is a complete absence of approved drugs for human use that specifically target and inhibit complement activation.

Based upon the available clinical and research data, it appears that in most acute and chronic settings, production of C3a and C5a is mediated by the activation of the complement pathways. In clinical settings, both C3a and C5a have been independently shown to be involved, developing suitable methods of inhibition for all pathways would be highly desirable. Both of the anaphylatoxins C3a and C5a are known to activate leukocytes and platelets. A frequent indicator of cellular activation is the cellular expression of CD11b on leukocytes, and CD62P on platelets. The release of several inflammatory molecules is triggered by the platelet-leukocyte binding mediated by these activation markers. One result of such conjugate formation is the removal of platelets from the circulation, a phenomenon that can contribute to the development of thrombocytopenia.

This invention is designed to inhibit the functional activity of C3b and its progressive effects in pathological conditions by use of an anti-C3b antibody.

SUMMARY

The present invention relates to a method of inhibiting C3b dependent complement activation by limiting C3 cleavage, as well as limiting binding of C3b to factor B and C3b to properdin. Antibodies that bind factor B to inhibit C3b binding to factor B are known. Antibodies that bind C3b and inhibit only alternative pathway activation are covered under this invention. C3 dependent complement activation can be inhibited by a C3 inhibitor molecule.

In one aspect of the invention, a C3 inhibitor molecule can comprise a whole or fragmented anti-C3 antibody. The fragmented anti-C3 antibody can be $F_{ab}$, $F_{(ab)2}F_v$, or single chain $F_v$. The anti-C3 antibody may be monoclonal, polyclonal, chimeric, or de-immunized and have the ability to bind C3 and its fragments. The present invention discloses the use of both anti-C3 antibodies and C3b antibodies for the treatment of several disease conditions that involve problematic complement system activation.

In another aspect, the invention relates to a method of inhibiting the adverse effects of C3b-dependent complement activation in a subject. The method includes administering to the subject an amount of a C3b inhibitory agent effective to inhibit C3b-dependent complement activation. In this context, the phrase "C3b-dependent complement activation" refers to activation of all three complement pathways. In some aspects of the invention, the C3b inhibitory agent is an anti-C3b antibody or fragment thereof and, in other aspects, the anti-C3b antibody has a reduced effector function. In still other aspects, the C3b inhibitory agent is a C3b inhibitory peptide. The methods, compositions, and medicaments of the invention are useful for inhibiting the adverse effects of C3b-dependent complement activation in vivo in mammalian subjects, including humans suffering from acute or chronic pathological conditions where inappropriate complement activation is involved in disease pathology.

In another aspect, the invention creates an anti-C3b antibody containing various combinations of complementarity determining regions 1 through 3 (CDRs 1 through 3), and framework regions (FR1 through FR4). The CDRs include light and heavy chain combinations. CDR-L1, CDR-L2, CDR-L3, CDR-H1, CDR-H2, CDR-H3 and the framework regions are used for the treatment of the above mentioned disease conditions for which alternative complement pathway plays a role. Antibodies that contain the CDRs in any order within the amino acid sequence of the variable region are covered under this invention. As such, this invention covers the sequences discussed as well as any sequence changes in the CDR or framework regions as long as 90% sequence identity is maintained. Such antibodies bind only the C3b molecule with a stoichiometry ratio of 1:1, which means that by using the antibody, one can evaluate the percent activation in a sample of plasma.

BRIEF DESCRIPTION OF THE DRAWINGS

FIG. 17 illustrates both the anti C3b heavy murine chain (SEQ ID NO. 1) and the anti C3b light murine chain (SEQ ID NO. 2).

FIG. 18 illustrates SEQ ID NO: 1 through SEQ ID NO: 10.

FIG. 19 illustrates SEQ ID NO: 11 through SEQ ID NO: 24.

FIG. 20 illustrates SEQ ID NO: 25 through SEQ ID NO: 32.

FIG. 21 illustrates SEQ ID NO: 33 through SEQ ID NO: 40.

FIG. 22 illustrates SEQ ID NO: 41 through SEQ ID NO: 48.

DETAILED DESCRIPTION

Figure 1:
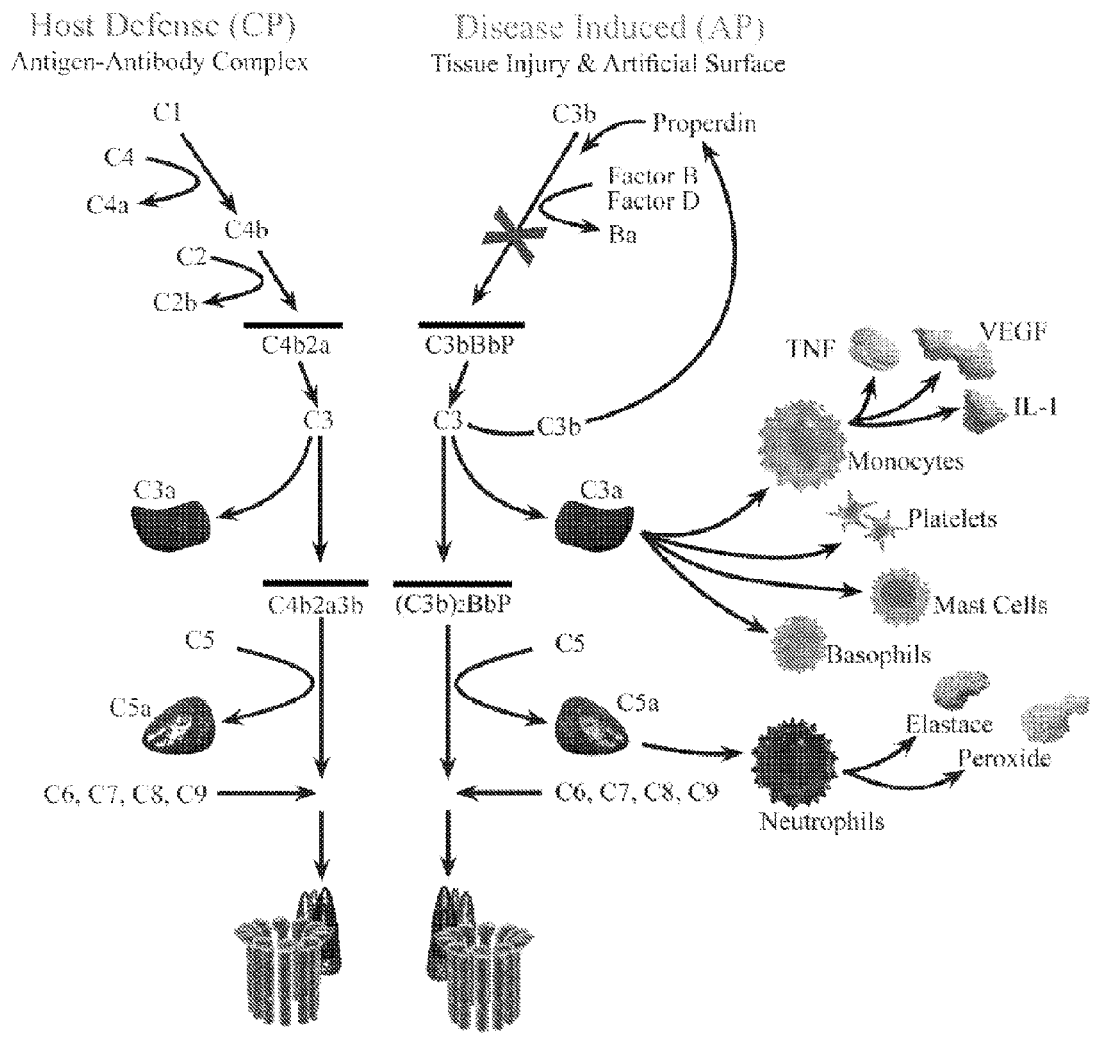
FIG. 1 illustrates the two complement pathways; the classical and the alternative complement pathways. This illustration separates the two pathways and not the convergence of the two pathways at C3b.
Figure 2:
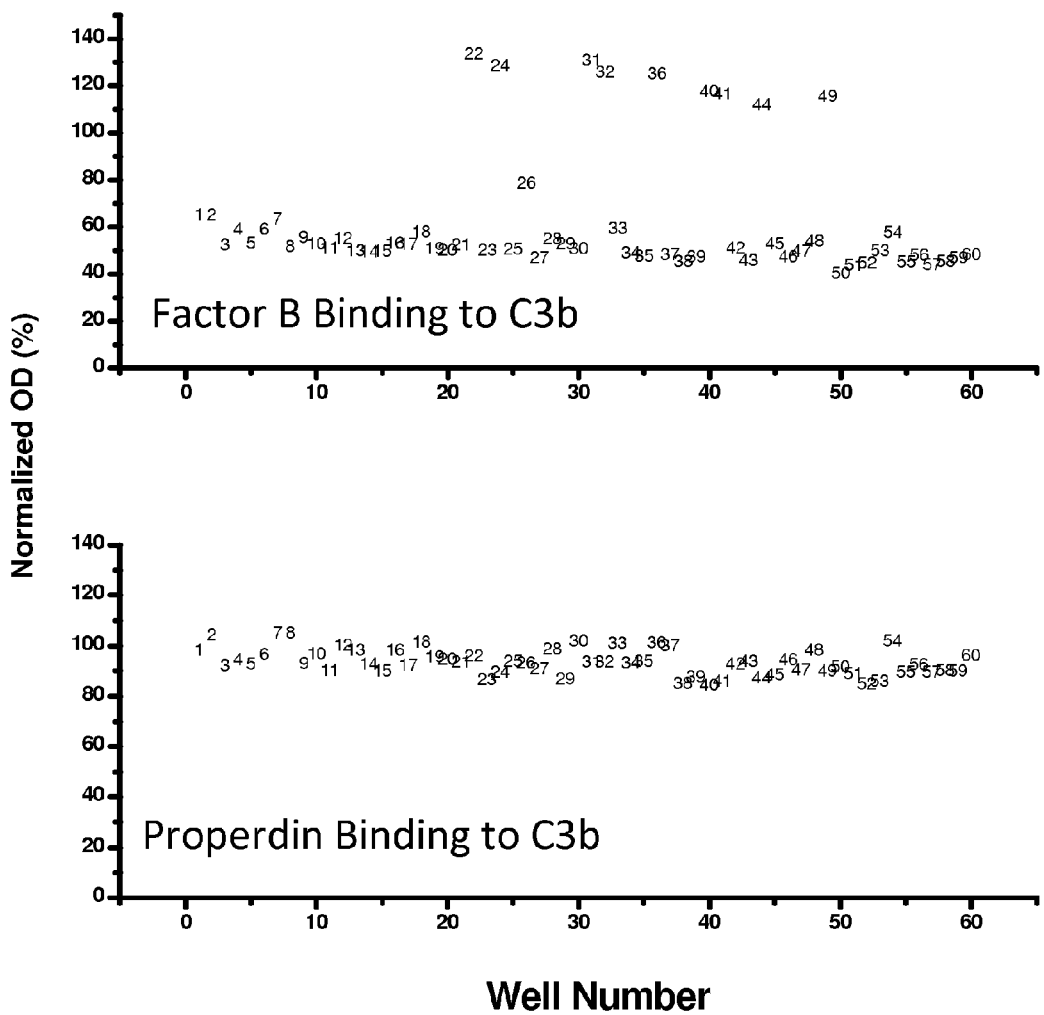
FIG. 2 illustrates the screening tests to identify and select clones that only inhibit the binding of C3b to B and not C3b to properdin.

Standard terminologies including those used by skilled in the art are common and standard and have been used throughout the application without reservation.

The following definitions are provided in order to provide clarity with respect to the terms as they are used in the specification and claims, in order to describe the present invention.

As used herein, the term "alternative pathway" refers to complement activation, which has traditionally been thought to arise from spontaneous proteolytic generation of C3b from complement factor C3 triggered, for example, by zymosan from fungal and yeast cell walls, lipopolysaccharide (LPS) from Gram-negative outer membranes, and rabbit erythrocytes, as well as from many pure polysaccharides, rabbit erythrocytes, viruses, bacteria, animal tumor cells, parasites and damaged cells.

As used herein, the term "antibody" encompasses antibodies and antibody fragments, which specifically bind to C3b or its polypeptides or portions, in which the antibody is derived from any antibody-producing mammal (e.g., a mouse, a rat, a rabbit, or a primate, including a human). Exemplary antibodies include polyclonal, monoclonal and recombinant antibodies; multi-specific antibodies (e.g., bi-specific antibodies), humanized antibodies; murine antibodies, chimeric (i.e., mouse-human, mouse-primate, primate-human), monoclonal antibodies, and anti-idiotype antibodies, as well as de-immunized antibodies, and may be any intact molecule or fragment thereof.

As used herein, the term "antibody fragment" refers to a portion derived from or related to a full-length anti-C3b antibody, generally including the antigen binding or variable region thereof. Illustrative examples of antibody fragments include Fab, Fab', F(ab)$_2$, F(ab')$_2$ and Fv fragments, scFv fragments, diabodies, linear antibodies, single-chain antibody molecules and multispecific antibodies formed from antibody fragments.

As used herein, the term "aptamer" refers to a nucleic acid molecule that binds to a particular target.

As used herein, the term "C3b-dependent complement activation" refers to complement activation that occurs via all possible pathways.

As used herein, the term "C3b inhibitory agent" refers to any agent that binds to or interacts with C3b and effectively inhibits C3b-dependent complement activation, including anti-C3b antibodies and C3b binding fragments thereof, natural and synthetic peptides. C3b inhibitory agents useful in the method of the invention may reduce C3b-dependent complement activation, therefore all activation, by greater than 20%. In one embodiment, the C3b inhibitory agent reduces complement activation by greater than 90%.

As used herein, a "chimeric antibody" is a recombinant protein that contains the variable domains and complementarity-determining regions derived from a non-human species (e.g., rodent) antibody, while the remainder of the antibody molecule is derived from a human antibody.

As used herein, the term "classical pathway" refers to both (1) complement activation of the C1-complex triggered by an antibody bound to a foreign particle and requires binding of the recognition molecule C1q, and also to (2) complement activation that occurs via antigen-antibody complex formation.

As used herein, a "humanized antibody" is a chimeric antibody that comprises a minimal sequence conforming to specific complementarity-determining regions derived from non-human immunoglobulin that is transplanted into a human antibody framework. Humanized antibodies are typically recombinant proteins in which only the antibody complementarity-determining regions are of non-human origin. As used herein, the term "lectin pathway" refers to complement activation that occurs via the specific binding of serum and non-serum carbohydrate-binding proteins including mannan-binding lectin (MBL) and the ficolins.

As used herein, the "membrane attack complex" ("MAC") refers to a complex of the five terminal complement components ($C_5$-$C_9$) that inserts into and disrupts membranes. MAC can also be referred to as C5b-9.

As used herein, a "subject" includes all mammals, including, but not limited to, dogs, cats, horses, sheep, goats, cows, rabbits, pigs, humans, non-human primates, and rodents. The alternative pathway can also provide an amplification loop for complement activation initially triggered via the classical and lectin pathways, in addition to its widely accepted role as an independent pathway for complement activation. In this alternative pathway-mediated amplification mechanism, the activation generated C3 convertase (C4b2b) from either the classical or the lectin complement cascades cleaves C3 into C3a and C3b, and thereby provides C3b that can participate in forming C3bBb, the alternative pathway C3 convertase.

As used herein, a "single-chain Fv" or "scFv" antibody fragment comprises the $V_H$ and $V_L$ domains of an antibody, wherein these domains are present in a single polypeptide chain. Generally, the Fv polypeptide further comprises a polypeptide linker between the $V_H$ and $V_L$ domains, which enables the scFv to form the desired structure for antigen binding.

The antibodies of the present invention are chimeric and humanized anti-C3b monoclonal antibodies (mAb), and antigen binding fragments for the treatment of human diseases. The antibody of the present invention can provide high affinity antibodies useful to meet this need. Anti-C3b monoclonal antibody of this invention can bind C3b and can inhibit C3b binding to factor B.

Both animal and plant derived anti-C3b monoclonal antibodies with characteristic CDR(s) that can bind C3b and can inhibit C3b binding to factor B are covered under the present application. CDRs that can have greater than 60% homology between CDRs of the antibody of the present invention are covered under the present application. A mouse monoclonal antibody used to generate the chimeric and humanized anti-C3b antibody is covered under the present application.

The antibody of the present invention differs from the prior art in that the present antibody (1) does not inhibit the classical complement pathway; (2) can bind the target protein with 0.33:1 molar equivalence; (3) can cross react with C3b but not C3; and (4) can inhibit the production of C3a, C5a, C5b-9 and TNF alpha. The present antibodies were generated against C3b and therefore do not cross react with C3a, which is a fragment of the intact C3 molecule.

C3b is part of the classical pathway and alternative pathway C3 convertase and therefore anti-C3b are expected to inhibit both pathway. Antibodies of this invention only inhibit the alternative and have no effect on the classical pathway activation. These antibodies can inhibit factor B binding to C3b without impacting the classical pathway. These antibodies can exclusively inhibit the alternative pathway without having an effect of the amplification loop on the classical pathway.

The antibodies of the present invention can inhibit the formation of new C3 convertase. These antibodies can inhibit factor B binding to C3b without impacting the classical pathway. These antibodies can exclusively inhibit the alternative pathway without having an effect of the amplification loop on the classical pathway.

Anti-C3b antibodies can be selected based on their ability to neutralize the C3b generated by the activation of the alternative pathway. The molar equivalence of 1:1 dictates that only 30% of the C3 is converted into C3b. The amount of total C3 activated was determined in whole blood inflammation model can range from 30% to 40%, to as high as about 50%.

Antibodies of the present invention can have no effect on classical pathway activation. Thus, the monoclonal antibodies of the present invention are able to not inhibit the classical pathway. The antibody mAb of the present invention can bind to a region on C3b that is only involved in AP activation via binding to factor B proteins.

Another aspect of the present invention relates to antibodies that comprise the heavy chain and light chain CDR1s, CDR2s and CDR3s of mAb, or combinations thereof. The amino acid sequences of the variable heavy chain CDR 1, 2 and 3 regions are shown in SEQ ID NOs: 12, 14, and 16, respectively. The amino acid sequences of the variable light chain CDR 1, 2 and 3 regions are shown in SEQ ID NO's: 19, 21, and 23, respectively wherein the antibody specifically binds human C3c and/or C3b.

The antibody can be, for example, a chimeric antibody, humanized antibody, human antibody, a humanized antibody or a chimeric antibody. The CDRs within the variable region may be 90% similar to about 99% similar.

Another aspect of the present invention is that the antibody can be an aptamer, or DNA fragments thereof. Similar to a full antibody, the aptamer can also bind to C3b to prevent formation of the PC3bBb complex or the BC3b complex.

The antibodies of the present invention, the CDRs of the present invention, and the framework of the present invention are listed in FIGS. 27-31.

The antibodies of the present invention can be therapeutic. Murine, chimeric, humanized, and primatized antibodies are currently considered therapeutic. However, with recent advances in science, the antibody can also be replaced by other types of antibody-like molecules in which the interaction of the antibody-like molecule may fall within a range of low pMole to high pMole to low nMole.

Both the chimeric antibodies and the humanized antibodies have human framework constant regions. The framework regions of the humanized and human are either natural human framework regions or non-natural human framework regions in order to increase the affinity and efficacy of the said CDR regions. Constant regions may or may not be present in the said antibody. Various methods are available to produce antibodies with and without the constant regions in plants, bacterial and mammalian cell system.

Functional activity of the anti-C3b antibody is defined as the ability of the anti-C3b antibody to inhibit AP activation without affecting the amplification loop of the classical pathway. These antibodies of the present invention can (1) inhibit B binding to C3b, (2) reduce PC3bBb formation/or C3bBb formation, (3) reduce concentration of free C3b, (4) reduce formation of C3b, (5) reduce formation of C3a, C5a and C5b-9, (6) reduces monocytes CD11b expression, (7) reduces neutrophil CD11b expression, (8) reduces platelet CD62 P expression, (9) reduces leukocyte-platelet conjugate formation, (10) reduces tumor necrosis factor alpha (TNF), and (11) reduces neutrophil elastase formation.

The present invention also provides methods of inhibiting the adverse effects of alternative pathway derived C3b-dependent complement activation. The C3b inhibitory agents can be used alone as a primary therapy or in combination with other methods as complement to enhance the benefits of other treatments.

The inhibitory agents can be small molecules, aptamers, DNA fragments, small peptides representing CDR domains, SiRNA. These inhibitory agents inhibit properdin binding to C5, C9, and C3b associated with C5.

The present invention proposes the new use of anti-C3b antibodies for the inhibition the complement biochemical cascade. The present invention describes the use of C3b as a therapeutic target for inhibiting cellular injury associated with all complement pathways.

Disease Conditions

In another aspect of the invention, the antibodies can be used to inhibit complement activation via the alternative pathway in vivo in subjects, including humans, suffering from an acute or chronic pathological injury. The present invention can be used in conjunction with the following diseases, disorders, injuries, and treatments, including but not limited to:

Extracorporeal circulation diseases and disorders: Post-cardiopulmonary bypass inflammation, post-operative pulmonary dysfunction, cardiopulmonary bypass, hemodialysis, leukopheresis, plasmapheresis, plateletpheresis, heparin-induced extracorporeal LDL precipitation (HELP), postperfusion syndrome, extracorporeal membrane oxygenation (ECMO), cardiopulmonary bypass (CPB), post-perfusion syndrome, systemic inflammatory response, and multiple organ failure.

Cardiovascular diseases and disorders: acute coronary syndromes, Kawaski disease (arteritis), Takayasu's arteritis, Henoch-Schonlein purpura nephritis, vascular leakage syndrome, percutaneous coronary intervention (PCI), myocardial infarction, ischemia-reperfusion injury following acute myocardial infarction, atherosclerosis, vasculitis, immune complex vasculitis, vasculitis associated with rheumatoid arthritis (also called malignant rheumatoid arthritis), systemic lupus erythematosus-associated vasculitis, sepsis, arteritis, aneurysm, cardiomyopathy, dilated cardiomyopathy, cardiac surgery, peripheral vascular conditions, renovascular conditions, cardiovascular conditions, cerebrovascular conditions, mesenteric/enteric vascular conditions, diabetic angiopathy, venous gas embolus (VGE), Wegener's granulomatosis, heparin-induced extracorporeal membrane oxygenation, and Behcet's syndrome.

Bone/Musculoskeletal diseases and disorders: arthritis, inflammatory arthritis, non-inflammatory arthritis, rheumatoid arthritis, juvenile rheumatoid arthritis, systemic juvenile rheumatoid arthritis, osteoarthritis, osteoporosis, systemic lupus erythematosus (SLE), Behcet's syndrome, and Sjogren's syndrome.

Transplantation diseases and disorders: transplant rejection, xenograft rejection, graft versus host disease, xenotransplantation of organs or grafts, allotransplantation of organs or grafts, and hyperacute rejection.

Eye/Ocular diseases and disorders: wet and dry age-related macular degeneration (AMD), choroidal neurovascularization (CNV), retinal damage, diabetic retinopathy, diabetic retinal microangiopathy, histoplasmosis of the eye, uveitis, diabetic macular edema, diabetic retinopathy, diabetic retinal microangiopathy, pathological myopia, central retinal vein occlusion (CRVO), corneal neovascularization, retinal neovascularization, retinal pigment epithelium (RPE), histoplasmosis of the eye, and Purtscher's retinopathy.

Hemolytic/Blood diseases and disorders: sepsis, systemic inflammatory response syndrome" (SIRS), hemorrhagic shock, acute respiratory distress syndrome (ARDS), catastrophic anti-phospholipid syndrome (CAPS), cold agglutinin disease (CAD), autoimmune thrombotic thrombocytopenic purpura (TTP), endotoxemia, hemolytic uremic syndrome (HUS), atypical hemolytic uremic syndrome (aHUS), paroxysmal nocturnal hemoglobinuria (PNH), sepsis, septic shock, sickle cell anemia, hemolytic anemia, hypereosinophilic syndrome, and anti-phospholipid syndrome (APLS).

Respiratory/Pulmonary diseases and disorders: asthma, Wegener's granulomatosis, transfusion-related acute lung injury (TRALI), antiglomerular basement membrane disease (Goodpasture's disease), eosinophilic pneumonia, hypersensitivity pneumonia, allergic bronchitis bronchiectasis, reactive airway disease syndrome, respiratory syncytial virus (RSV) infection, parainfluenza virus infection, rhinovirus infection, adenovirus infection, allergic bronchopulmonary aspergillosis (ABPA), tuberculosis, parasitic lung disease, adult respiratory distress syndrome, chronic obstructive pulmonary disease (COPD), sarcoidosis, emphysema, bronchitis, cystic fibrosis, interstitial lung disease, acute respiratory distress syndrome (ARDS), transfusion-related acute lung injury, ischemia/reperfusion acute lung injury, byssinosis, heparin-induced extracorporeal membrane oxygenation, anaphylactic shock, and asbestos-induced inflammation.

Central and Peripheral Nervous System/Neurological diseases and disorders: multiple sclerosis (MS), myasthenia gravis (MG), myasthenia gravis, multiple sclerosis, Guillain Bane syndrome, Miller-Fisher syndrome, stroke, reperfusion following stroke, Alzheimer's disease, multifocal motor neuropathy (MMN), demyelination, Huntington's disease, amyotrophic lateral sclerosis (ALS), Parkinson's disease, degenerative disc disease (DDD), meningitis, cranial nerve damage from meningitis, variant Creutzfeldt-Jakob Disease (vCJD), idiopathic polyneuropathy, brain/cerebral trauma (including, but not limited to, hemorrhage, inflammation, and edema), and neuropathic pain.

Trauma-induced injuries and disorders: hemorrhagic shock, hypovolemic shock, spinal cord injury, neuronal injury, cerebral trauma, cerebral ischemia reperfusion, crush injury, wound healing, severe burns, and frostbite.

Renal diseases and disorders: renal reperfusion injury, poststreptococcal glomerulonephritis (PSGN), Goodpasture's disease, membranous nephritis, Berger's Disease/IgA nephropathy, mesangioproliferative glomerulonephritis, membranous glomerulonephritis, membranoproliferative glomerulonephritis (mesangiocapillary glomerulonephritis), acute postinfectious glomerulonephritis, cryoglobulinemic glomerulonephritis, lupus nephritis, Henoch-Schonlein purpura nephritis, and renal cortical necrosis (RCN).

Reperfusion injuries and disorders of organs: including but not limited to heart, brain, kidney, and liver.

Reproduction and urogenital diseases and disorders: painful bladder diseases and disorders, sensory bladder diseases and disorders, spontaneous abortion, male and female diseases from infertility, diseases from pregnancy, fetomaternal tolerance, pre-eclampsia, urogenital inflammatory diseases, diseases and disorders from placental dysfunction, diseases and disorders from miscarriage, chronic abacterial cystitis, and interstitial cystitis.

Skin/Dermatologic diseases and disorders: burn injuries, psoriasis, atopic dermatitis (AD), eosinophilic spongiosis, urticaria, thermal injuries, pemphigoid, epidermolysis bullosa acquisita, autoimmune bullous dermatoses, bullous pemphigoid, scleroderma, angioedema, hereditary angioneurotic edema (HAE), erythema multiforme, herpes gestationis, Sjogren's syndrome, dermatomyositis, and dermatitis herpetiformis.

Gastrointestinal diseases and disorders: Crohn's disease, Celiac Disease/gluten-sensitive enteropathy, Whipple's disease, intestinal ischemia, inflammatory bowel disease, and ulcerative colitis.

Endocrine diseases and disorders: Hashimoto's thyroiditis, juvenile lymphocytic thyroiditis, stress anxiety, and other diseases affecting prolactin, growth or insulin-like growth factor, adrenocorticotropin release, pancreatitis, Addison's disease, diabetic conditions including, but not limited to, type 1 and type 2 diabetes, type I diabetes mellitus, sarcoidosis, diabetic retinal microangiopathy, non-obese diabetes (IDDM), angiopathy, neuropathy or retinopathy complications of IDDM or Type-2 diabetes, and insulin resistance.

Treatment of Malignancies: diseases and disorders arising from chemotherapeutics and radiation therapy.

In another example of the invention, the antibodies of the present invention treat injuries, for example ischemia reperfusion injury (I/R). The pathophysiology of I/R injury is complex, with at least two major factors contributing to the process: complement activation and neutrophil stimulation with accompanying oxygen radical-mediated injury.

Through investigation, growing evidence identifies complement as a pivotal mediator in I/R injury as inhibition of complement activation has been successful in limiting tissue damage and injury in numerous I/R animal models. In early studies, C3 depletion was obtained following infusion of cobra venom factor, reported to be beneficial during I/R in kidney and heart. However, the soluble form of complement receptor 1 (sCR1) was the first complement-specific inhibitor utilized for the prevention of myocardial I/R injury decreased deposition of C5b-9 complexes along the coronary endothelium and decreased leukocyte infiltration after reperfusion was associated with sCR1 treatment during myocardial I/R attenuates infarction Animals genetically deficient in C3 have less local tissue necrosis after skeletal muscle or intestinal ischemia.

The membrane attack complex is the most significant vehicle of complement-directed injury and studies in animals with a C5-deficiency have shown decreased local and remote injury in models of I/R injury. An inhibitor of complement activation, soluble Crry (complement receptor-related gene Y), has shown effectiveness against injury when given both before and after the onset of murine intestinal reperfusion. In a model of skeletal muscle ischemia, the use of soluble complement receptor 1 (sCR1) also reduced muscle injury when given after the start of reperfusion. In a porcine model of myocardial I/R, animals treated with monoclonal antibody ("MoAb") to the anaphylatoxin C5a prior to reperfusion showed attenuated infarction. Rats treated with C5 MoAb demonstrated attenuated infarct size, neutrophil infiltration, and apoptosis in the myocardium.

In another example, the C3b inhibitory agent may be administered prior to and/or during and/or after reperfusion for some disorders, including, but not limited to: aortic aneurism repair, organ transplant or reattachment of severed or traumatized limbs or digits. The C3b inhibitory agent can be administered in various ways by intra-arterial, intracranial, intravenous, subcutaneous, intramuscular, or other parenteral administration. Potentially orally for non-peptidergic inhibitors, and most suitably by intra-arterial or intravenous administration. Administration may be repeated periodically as determined by a physician for optimal therapeutic effect.

Example 1

Unless stated otherwise, all reagents were of high grade available. All complement proteins, alternative and classical pathway buffers, detection antibodies, and erythrocytes were from Complement Technologies (Tyler, Tex.) or Quidel Corporation (San Diego, Calif.). Flow cytometry antibodies were from BD Biosciences, San Jose, Calif.TMB substrate was from Kirkegaard & Perry Limited, Gaithersburg, Md. All secondary antibodies were from American Qualex, San Clemente, Calif., BSA and other reagents were all from Sigma-Aldrich, St Louise, Mo.

ELISA plate readers (SpectraMax® 190 and 250) were from Molecular Devices, and Flow Cytometer was FACSCalibur™. Varity 3D program was used for data analyses, Curve fittings were done using MicroCal Origin® program. Hemolysis kinetic assay was run using SpectraMax®, Molecular Devices., ELISA plates were from Corning Costar, Lowell, Mass.

Humanized and chimeric antibodies contain the CDRs of the parent murine monoclonal antibody, sequence (SEQ ID NO: 1 and SEQ ID NO: 2), which is present in this application. Mice were injected with human C3b (Complement Technology, Tyler, Tex.) and mouse serum was screened for C3b binding and AP inhibitory activity. Spleen cells from properdin positive mouse were fused with myeloma cells using standard procedures. The fusion cells were cloned into a single cell population using limiting dilution technique. The cells in 96 well plate were allowed to grow to supernatant was tested using properdin binding and alternative pathway inhibition. Cells that block AP activation were identified and further screened using those that inhibit C5b-9 formation. These clones were categorized under 7D11 which inhibit Factor B binding to C3b with high affinity. Intact IgG was converted into Fab, Fab', $Fab_2$' fragments using proteolytic digestion. The hybridoma cell line that produces 7D11 deposited with the American Type Culture Collection ("ATCC") with PTA-8806

Anti-C3b IgG Binds Human C3b and C3c with High Affinity but does not Bind C3dg

The affinity of anti-C3b IgG to C3b is in the range of low pM to low nM. The antibody and its fragments bind C3b and C3c with high affinities. Polystyrene microtiter plates were coated with human C3b in phosphate buffered saline (PBS) overnight at 4° C. After aspirating the C3b solution, the wells were blocked with 1% bovine serum albumin (BSA) (Sigma-Aldrich, St. Louis, Mo.) in PBS for 1 hour at room temperature. Wells without peptide or C3b coating served as background controls. Aliquots of monoclonal anti C3b antibody IgG, Fab2, and Fab in blocking solution were added to the C3b coated wells and allowed to incubate for 1 hour to allow binding to occur. Following a 1 hour incubation period at room temperature, the plate was rinsed with PBS five times and incubated with peroxidase-conjugated goat anti-mouse monoclonal antibody. Following this incubation, the plate was rinsed and the bound peroxidase was identified using TMB reagent.

Figure 3:
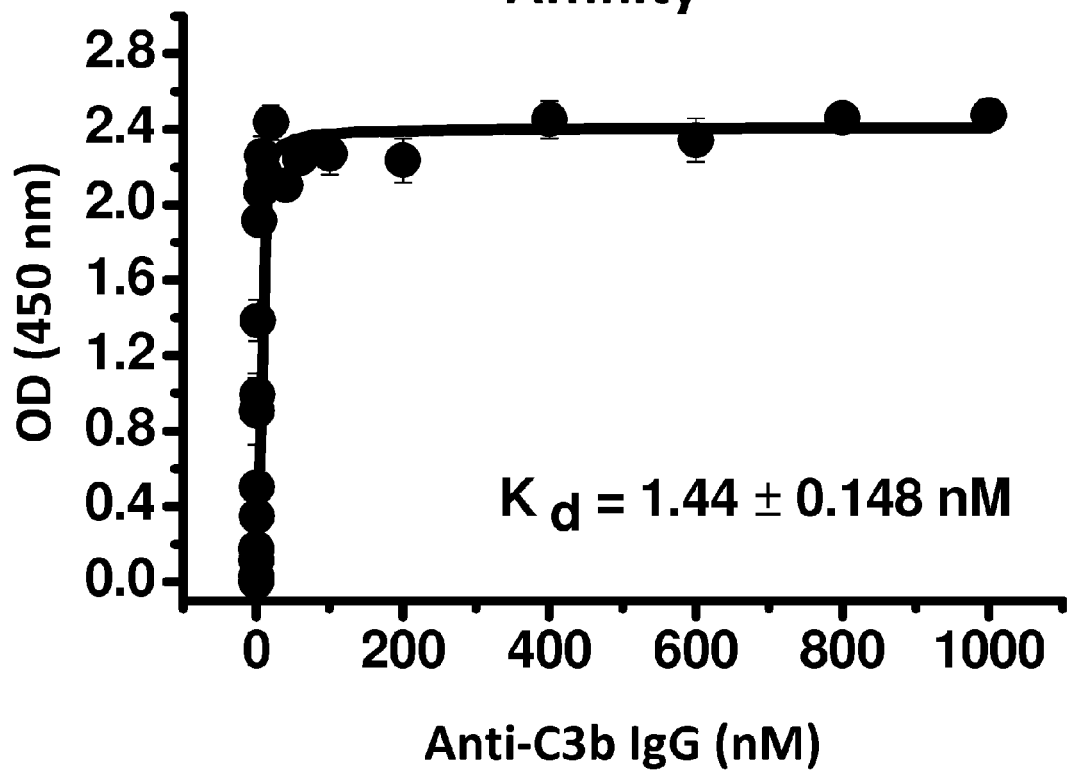
FIG. 3 illustrates the saturation binding affinity of anti-C3b to substrate-bound C3b.
Figure 4:
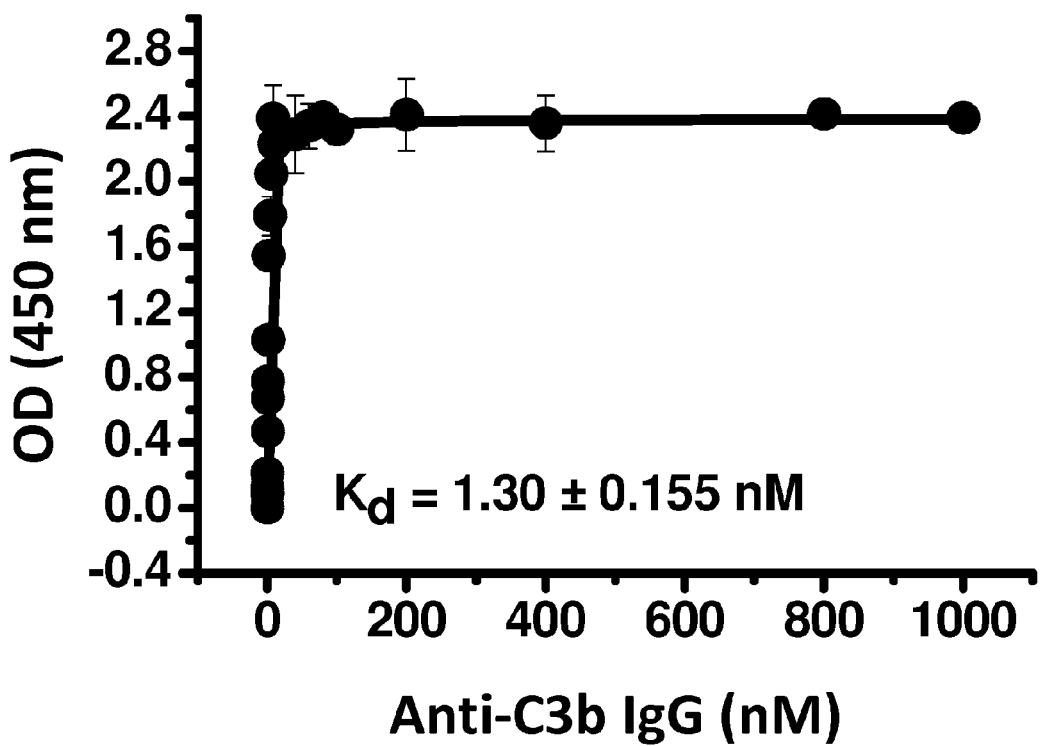
FIG. 4 illustrates the binding of anti-C3b to C3c with high affinity.
Figure 5:
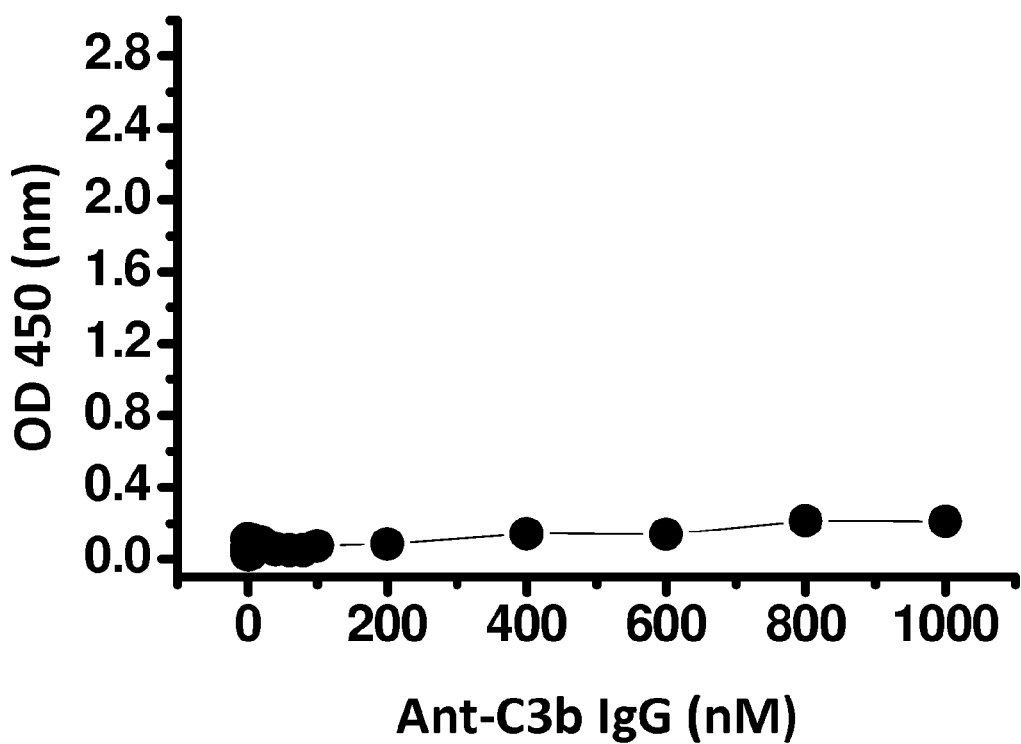
FIG. 5 illustrates the absence of binding of anti-C3b to C3dg.
Figure 6:
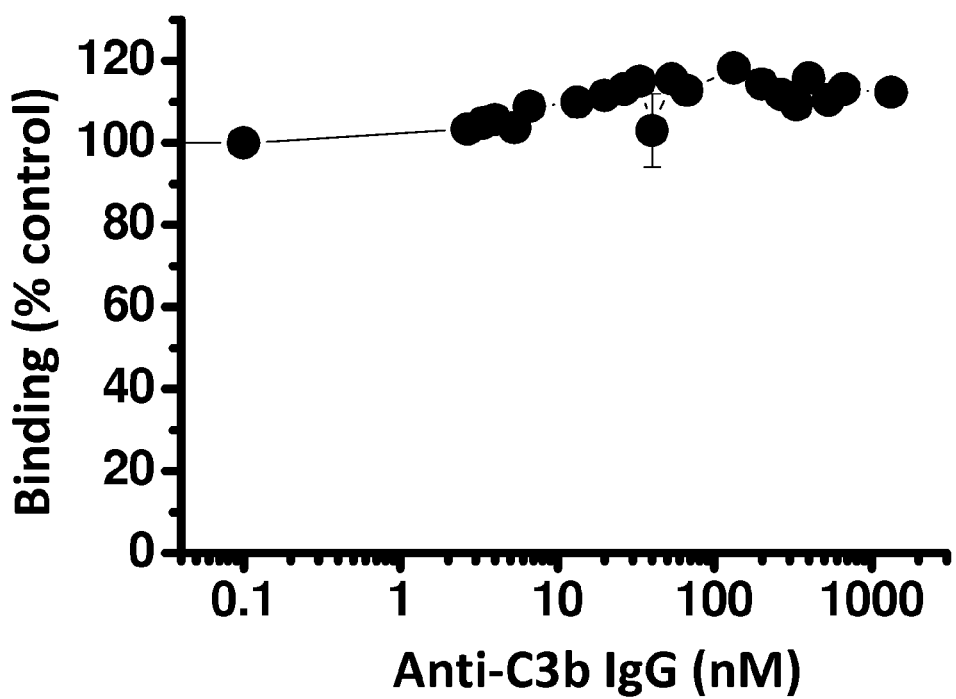
FIG. 6 illustrates the lack of inhibition of properdin binding to C3b.

As shown, anti-C3b binds C3b (FIG. 3) and C3c (FIG. 4). The antibody binding site does not reside in C3dg (FIG. 5).

Example 2

Anti-C3b IgG does not Inhibit Properdin C3b Interaction

The affinity of anti-C3b IgG to C3b is in the range of low pM to low nM. The antibody and its fragments bind C3b and C3c with high affinities. These antibodies and its fragments do not inhibit properdin binding to C5. Polystyrene microtiter plates were coated with human C3b in phosphate buffered saline (PBS) overnight at 4° C. After aspirating the C3b solution, the wells were blocked with 1% bovine serum albumin (BSA) (Sigma-Aldrich, St. Louis, Mo.) in PBS for 1 hour at room temperature. Wells without peptide or C3b coating served as background controls. Aliquots of monoclonal anti C3b antibody IgG, Fab2, and Fab in blocking solution containing 2 nM biotinylated properdin were added to the C3b coated wells and allowed to incubate for 1 hour to allow binding to occur. Following a 1 hour incubation period at room temperature, the plate was rinsed with PBS five times and incubated with peroxidase-conjugated neutavidin. Following this incubation, the plate was rinsed and the bound peroxidase was identified using TMB reagent.

As shown, anti-does not inhibit properdin binding to C3b suggesting that it is a different site other than the properdin site on C3b that is involved in binding.

Example 3

Anti-C3b IgG, F(ab')2, and Fab Inhibit Alternative Pathway (AP) Dependent Rabbit Red Blood Cell (rRBC) Lysis This erythrocyte lysis assay is based on the formation of terminal complement complex on the surface of the rRBC. As a result, the rRBCs are lysed. The progressive decrease in light scatter at 900 nm is a direct measure of erythrocyte lysis. Typically, rRBC(s) are incubated in normal human serum in gelatin veronal buffer containing 5 mM $MgCl_2$. Under these conditions, the surface of rRBC triggers the activation of alternative pathway in normal human serum. The alternative pathway activation leads to the formation of C5b-9 complex on the surface of the rRBC(s). Agents that inhibit the formation of C5b-9 complexes are expected to inhibit cellular lysis. To evaluate the effect of anti-C3b antibody and fragments thereof, various concentrations of IgG, F(ab')$_2$, and Fab were incubated with normal human serum (10% NHS) in AP buffer at 37° C. with a fixed concentration of rabbit erythrocytes in a temperature controlled ELISA plate reader capable of reading at 900 nm. A progressive decrease in light scatter (due to lysis of intact cells) was measured at 900 nm as a function of time. The data were recorded and analyzed with a Spectra-Max® 190 plate reader and SoftMax® software. For calculation total inhibition was calculated at each concentration of the IgG, F(ab')2, and Fab, and the results were expressed as a % of unlysed controls. Data at each concentration was plotted in a sigmoidal plot with MicroCal Origin® Software.

Figure 7:
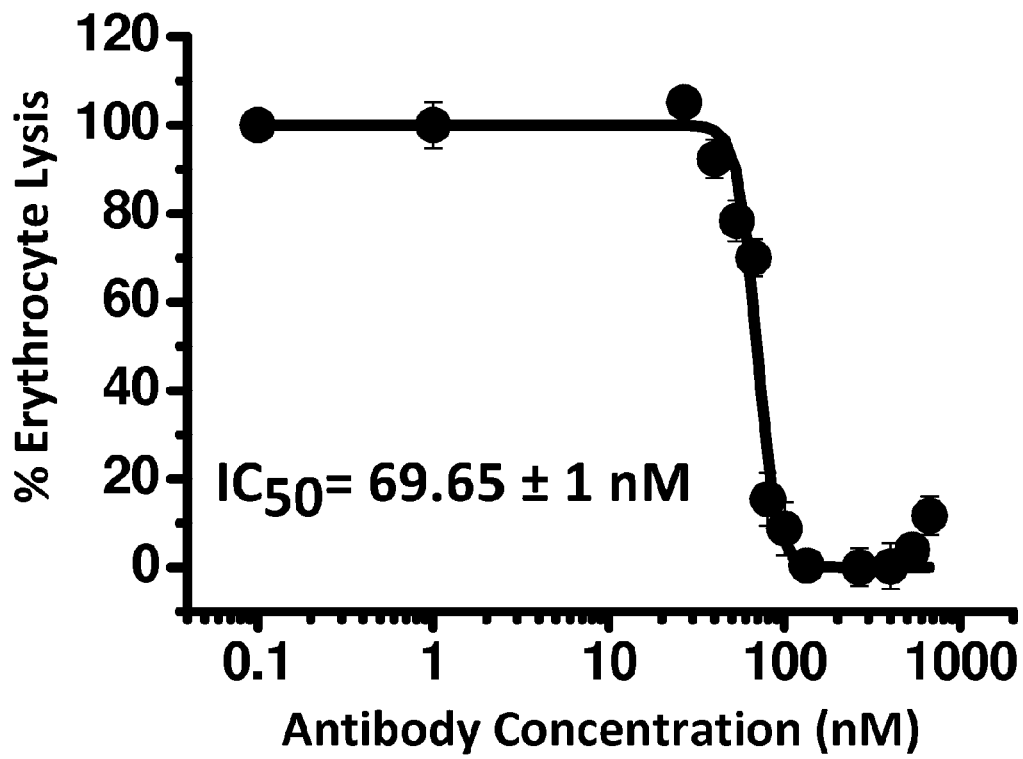
FIG. 7 illustrates that anti-C3b inhibits the alternative complement pathway in normal human serum.

As shown in FIG. 7 IgG anti-C3b inhibits AP dependent hemolysis of rRBC in normal human serum with an IC50 of inhibiting erythrocyte lysis. The antibodies are able to inhibit lysis with an IC50 of approximately 69 nM.

Example 4

Anti-C3b Monoclonal Antibodies do not Inhibit the Classical Pathway Activation

Monoclonal antibodies of the present invention do not inhibit the classical pathway which is required for host defense. Antibody sensitized sheep erythrocytes were incubated with 1% or 10% normal human serum in gelatin veronal buffer containing calcium (5 mM $CaCl_2/MgCl_2$) buffer. Antibody sensitized sheep cells activate the classical pathway. As a result, C5b-9 is formed on the surface of the erythrocyte accused lysis. We tested 1% and 10% normal human serum. Under both conditions, anti-C3b inhibited erythrocyte lysis. In a typical assay, erythrocytes are incubated in 1%/10% normal human serum in CP buffer to allow complement activation to occur. As a result of CP activation, C5b-9 is formed on the surface of erythrocytes causing cellular lysis. The progressive decrease in light scattering due to cellular lysis is measured at 700 nm as a function of time.

Figure 8:
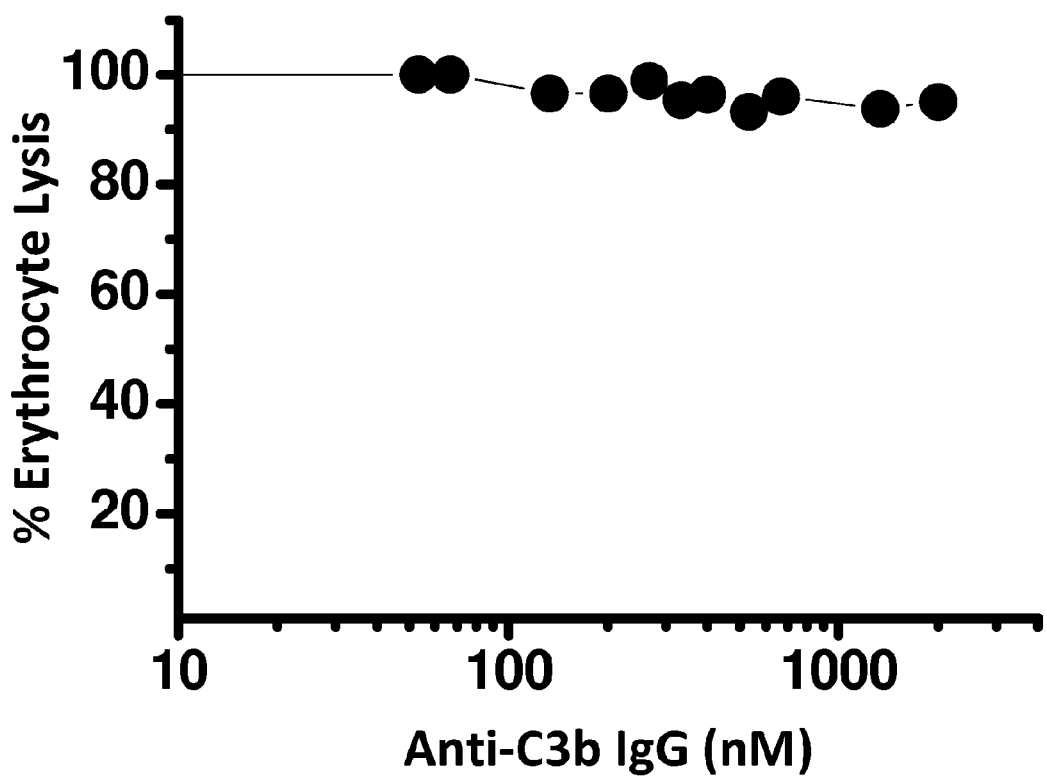
FIG. 8 illustrates that anti-C3b does not inhibit the classical complement pathway.

As shown in FIG. 8, anti-C3b IgG does not inhibit the lysis of the antibody sensitized sheep cells at both serum concentration. No serum control did not show any effect. These results suggest that anti-C3b antibodies are capable of selectively inhibiting the alternative complement pathway without affecting the classical pathway activation.

Example 5

Figure 9:
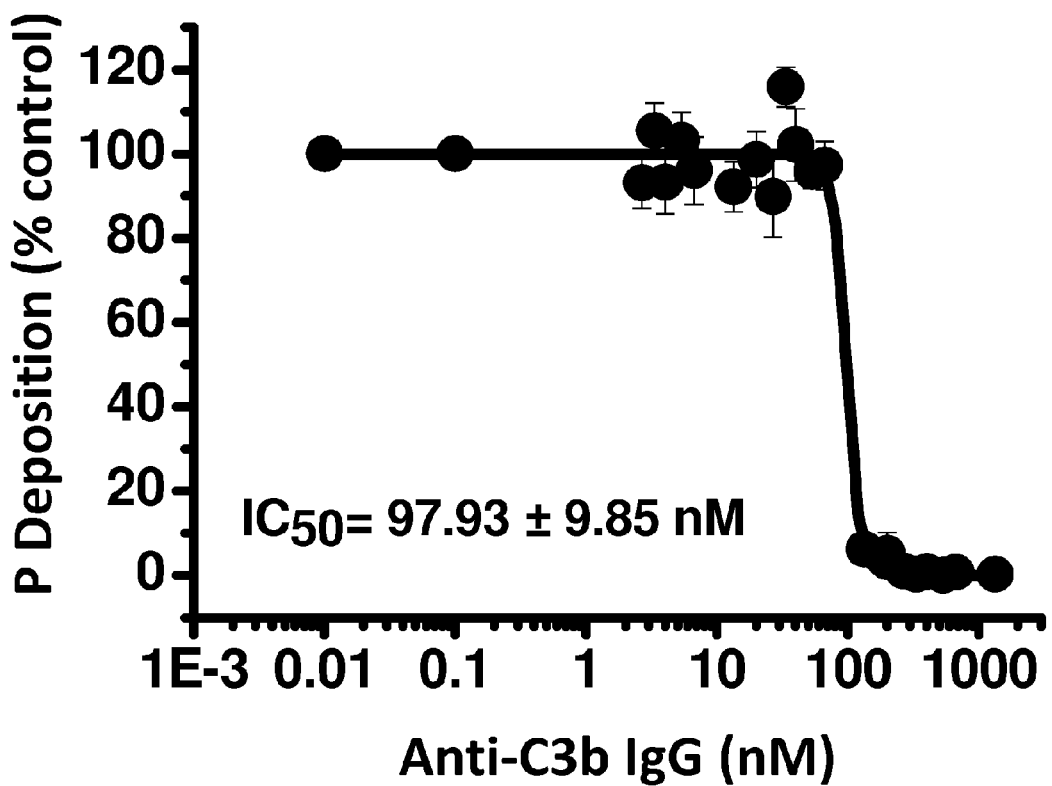
FIG. 9 illustrates that anti-C3b IgG inhibits the formation of C3 convertase by inhibiting the formation of properdin containing complexes PC3bBb.
Figure 10:
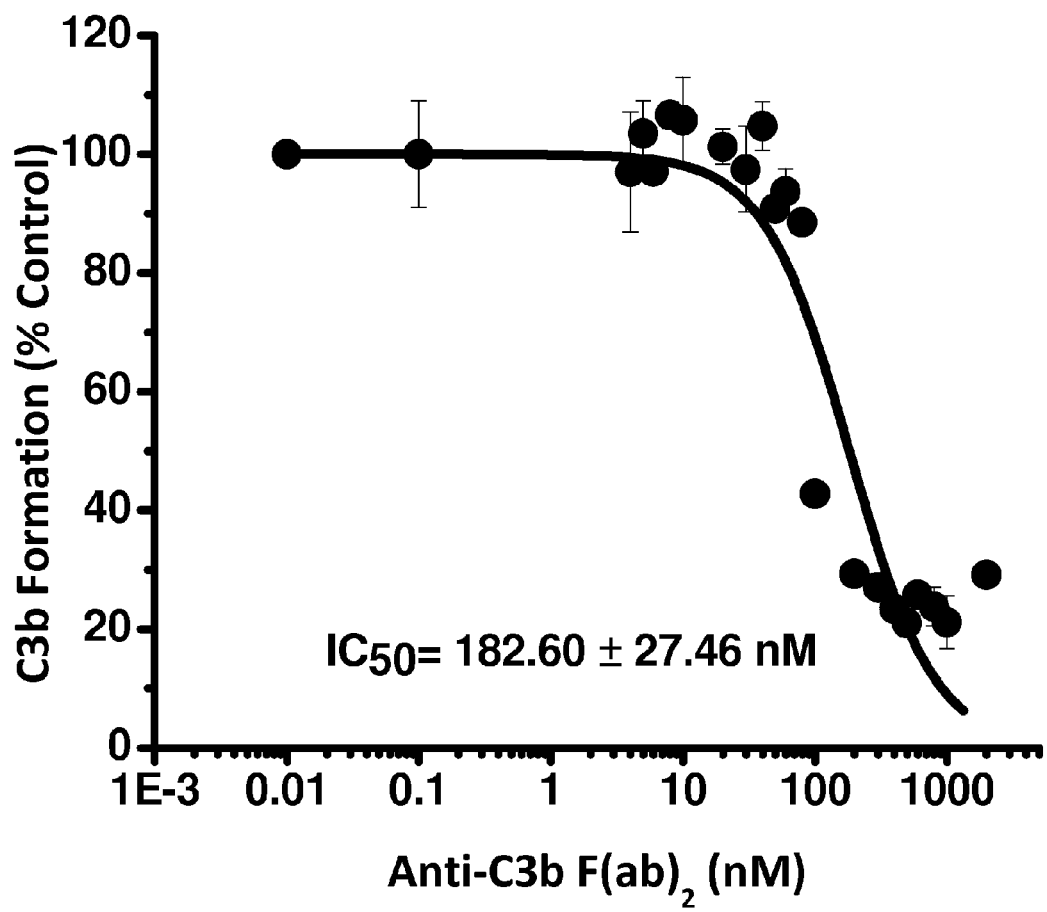
FIG. 10 illustrates that anti-C3b Fab2 inhibits the formation of C3 convertase by inhibiting the formation of newly formed C3b.

Anti-C3b IgG and Fragments Thereof. Inhibit the Formation of C3 Convertase (PC3bBb) of Alternative Complement Pathway Alternative complement pathway is activated in normal human serum by lipopolysaccharide from Salmonella typhosa. We have utilized this paradigm to demonstrate whether anti-properdin antibody of this invention would inhibit the formation of PC3bBb. We measured the deposition of P, C3b, Bb, and C5b-9 in the presence and absence the anti-properdin antibody and fragments thereof. The formation of C3 and C5 convertases were detected with appropriate antibodies. In the presence of anti-properdin antibodies, a dose dependent inhibition of C3 and C5 convertase formation was noticed. In a typical assay, polystyrene microtiter plate wells were coated with LPS (Lipopolysaccharide from Salmonella Typhosa) at 2 μg/50 μl in PBS overnight. The wells were incubated with 1% BSA in PBS to block the unoccupied sites in the wells. Following a 2-hour blocking at room temperature and rinsing with PBS, normal human serum (10%) in an AP buffer was mixed with varying concentrations of the antibody and fragments. The mixture was incubated onto LPS coated wells. The plate was incubated for 2 hours at 37° C. to allow complement AP activation to occur. Following incubation, the plates were extensively washed with PBS, and components of the C3 convertase were detected with the appropriate antibodies. We detected C3b with rabbit anti-human C3c at 1:2000 in blocking solution, goat anti-human P at 1:2000 in blocking solution and goat anti-human factor Bb at 1:500 in blocking solution and HRPO conjugated anti-huma C5b-9 at 1:2000 in blocking solution. Plates were incubated with their respective antibodies for 1-hour at room temperature. Following the incubation, the plates were rinsed with PBS and the bound antibodies were detected with peroxidase labeled goat anti-rabbit at 1:2000 for C3b and peroxidase labeled rabbit anti-goat at 1:2000 in blocking solution for P detection. All plates were developed with TMB following extensive washing with PBS. The blue color was quenched with 1 M orthophosphoric acid. FIG. 9 demonstrates a dose dependent inhibition of P deposition.

FIG. 9 shows a dose dependent deposition of P deposition, FIG. 9 shows a dose dependent deposition of formation deposition. These data provide direct evidence that anti-C3b monoclonal antibodies prevent convertase formation and inhibit AP activation.

Example 6

Anti-C3b Inhibits Alternative Complement and Cellular Activation in Whole Blood

Anti-C3b antibodies can be used in an extracorporeal circulation procedure, such as cardiopulmonary bypass (CPB) and or dialysis procedures on a subject. In these procedures, circulating blood can be passed from a blood vessel of the subject, through a conduit and back to a blood vessel of the subject. The conduit can have a luminal surface comprising a material capable of causing at least one of complement activation, platelet activation, leukocyte activation, or platelet-leukocyte adhesion in the subject's blood. An anti-C3b antibody can be introduced into the subject's bloodstream in an amount effective to reduce at least one of complement activation, platelet activation, leukocyte activation, or platelet-leukocyte adhesion resulting from passage of the circulating blood through the conduit. The blood of the subject can be passed through the conduit before and/or during and/or after step introduction of the anti-C3b antibody or fragment thereof. Preferably, the anti-properdin antibody reduces the alternative pathway-dependent conversion of complement component C3 into complement components C3a and C3b, and/or the alternative pathway-dependent formation of C5b-C9, and/or the alternative pathway-dependent leukocyte activation.

The whole blood tubing loop model demonstrates biomaterial induced AP activation. This model mimics the extracorporeal circulation models of cardiopulmonary bypass and dialysis. Freshly isolated human blood was collected in a 50 mL polypropylene tube containing 5 units/mL of heparin as an anticoagulant. The heparinized blood was diluted with plasmalyte-148 containing various concentrations of anti-C3b. Tubing loops were half filled with 2.0 mL of diluted blood and vertically rotated at 37 degrees in polyethylene tubes used in extracorporeal procedures. After incubation and rotation, blood samples were transferred into 2.0 mL tubes. Aliquots of these blood samples were also saved for flow cytometry. The remaining blood volume was centrifuged (4000×g for 5 minutes at 4° C.) and the plasma samples were collected. Inhibition of Complement activation: Plastic surface of the tubing loop activates alternative pathway. As a result C3a, C5a, and C5b-9 are formed. Elevated levels above the baseline can be measured using commercial ELISA methods. The plasma samples following the tubing loop were evaluated for complement activity utilizing C3a & C5b-9 kits (Quidel), and the rabbit erythrocyte-lysis assay. As a result of biomaterial surface induced alternative pathway activation, C3 is converted into C3a and C3b. Likewise, C5 is cleaved into C5a and C5b.

Figure 11:
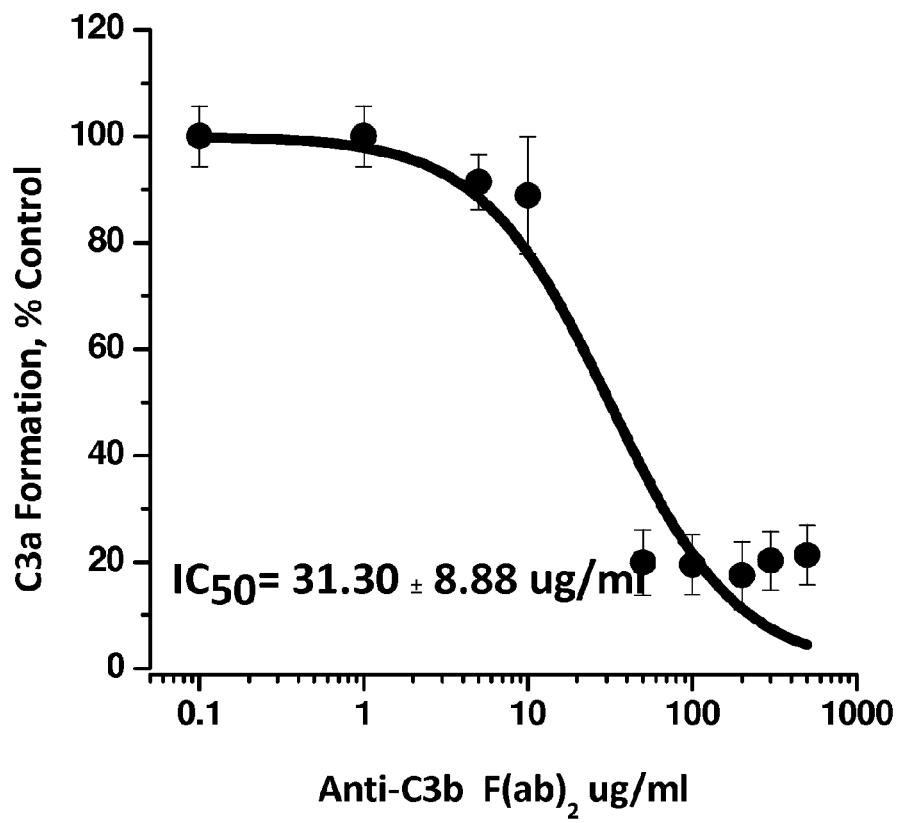
FIG. 11 illustrates that anti-C3b Fab2 inhibits the formation of C3a in whole blood model of inflammation.
Figure 12:
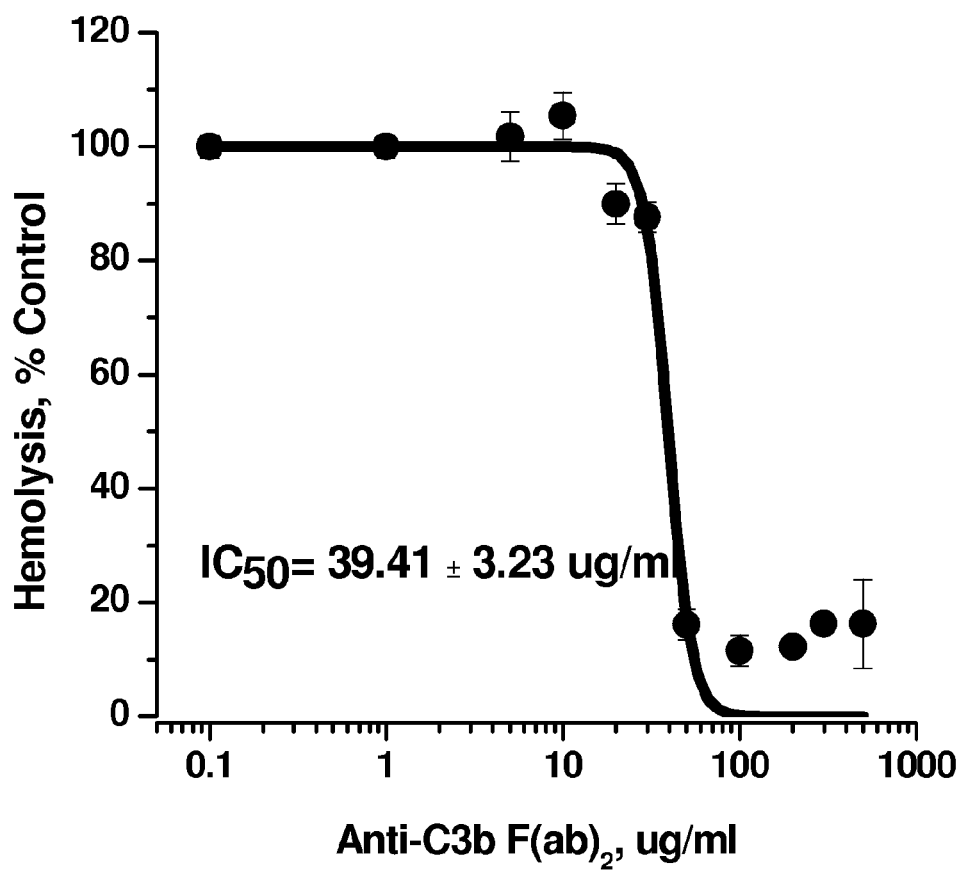
FIG. 12 illustrates that anti-C3b Fab2 inhibits the formation of SC5b-9 in whole blood inflammation model.

FIG. 11 demonstrates a dose dependence inhibition of C3a formation with an $IC_{50}$ of 31 µg/ml. Anti-C3b inhibited C5b-9 formation as shown in FIG. 12.

Example 7

Inhibition of TNF-α Formation by NM9405 Following Extracorporeal Circulation

Activated monocytes release TNF-α, an inflammatory mediator of inflammation. Monocytes are activated via C3a. Anti-C3b treated blood samples in the extracorporeal circulation demonstrate a dose-dependent inhibition of TNF-alpha.

TNF-α is a potent inflammatory cytokine that has been implicated in several disease pathologies. TNF-α is pro-inflammatory cytokine that recruits other inflammatory mediators to exacerbate the inflammatory response and causes apoptosis and cell and tissue damage. TNF-α inhibition is a key marker for inhibition of inflammatory responses. Validated anti-TNF drugs and biologics have provided significant benefit in the disease. Following the tubing loop circulation, plasma samples were also subjected to TNF-alpha assay. (BD-Biosciences).

Figure 13:
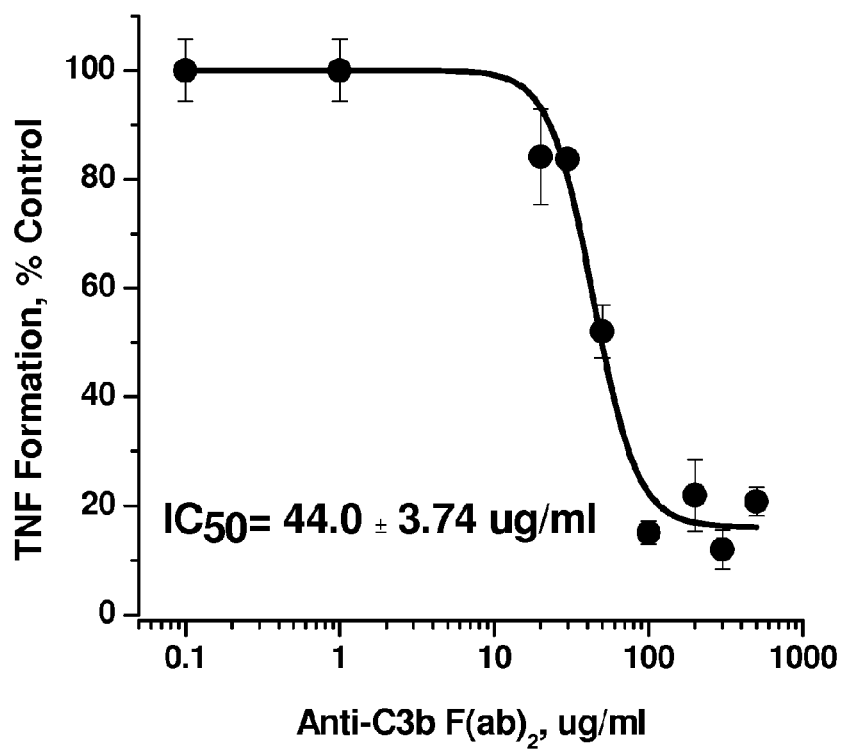
FIG. 13 illustrates that anti-C3b Fab2 inhibits the formation of TNF-alpha in whole blood inflammation model.

As shown in FIG. 13, anti-C3b demonstrates a dose dependent inhibition of TNF-alpha formation with an $IC_{50}$ observed at about 44 µg/ml.

Example 8

Production of Monoclonal Antibodies

Production of murine monoclonal antibodies has been described by those skilled in the art and has been a common practice. Typically, the antigen, in this case C3b protein was administered in the mice in a manner to produce monoclonal antibodies. Humanized and chimeric antibodies has been produced by CDR grafting and using the generic constant regions. The murine monoclonal antibodies specific to C3b were selected based on the alternative pathway inhibition assay. C3b is also the part of the classical pathway, surprisingly this anti-C3b antibody does not inhibit the classical pathway and only inhibits the alternative pathway. Murine antibody was converted into a chimeric and humanized antibody.

Example 9

Chimeric Anti-C3b Monoclonal Antibodies Bind C3b

Chimeric anti-C3b antibody Fab binds substrate-bound C3b. Polystyrene microtiter plate wells (96-well medium binding plates, Corning Costar, Cambridge, Mass.) were coated with C3b (2 µg/50 µl/well, complement technology, Tyler, Tx) in phosphate-buffered saline (PBS) pH 7.4 overnight at 4° C. After aspirating the C3b solution, wells are blocked with PBS containing 1% bovine serum albumin (BSA; Sigma Chemical) for 1 h at room temperature. Wells without C3b coating serve as the background controls. Aliquots of chimeric antibodies in blocking solution were added to C3b coated ELISA wells. The amount of bound chimeric antibody was detected with peroxidase conjugated anti-human IgG light chain antibody.

Figure 14:
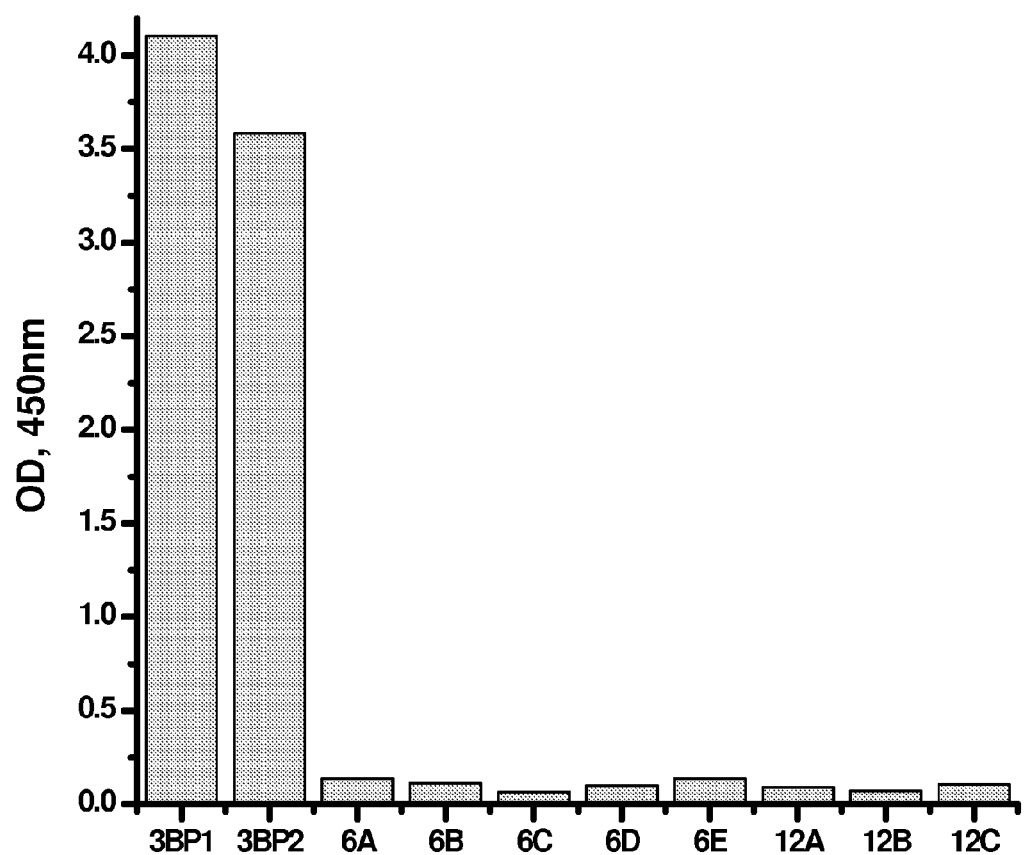
FIG. 14 illustrates that chimeric anti-C3b Fab binds to substrate-bound C3b.
Figure 15:
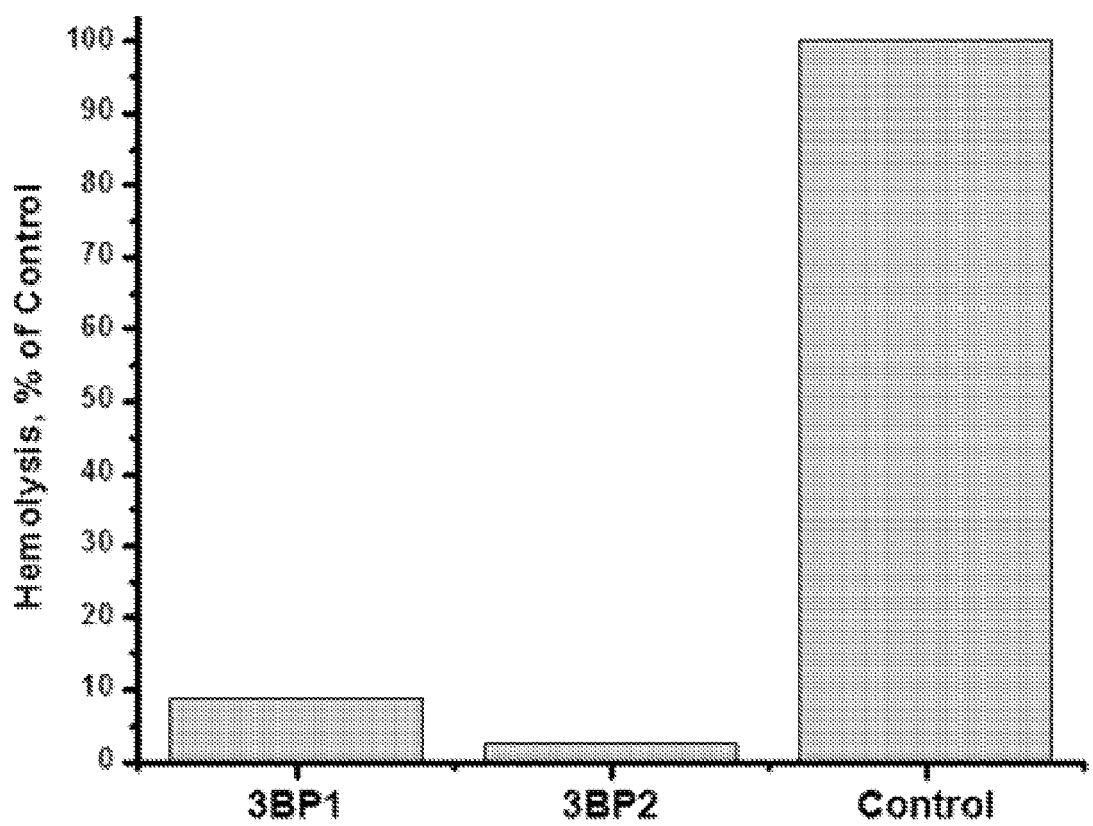
FIG. 15 illustrates that chimeric anti-C3b Fab inhibits AP activation in normal human serum.
Figure 16:
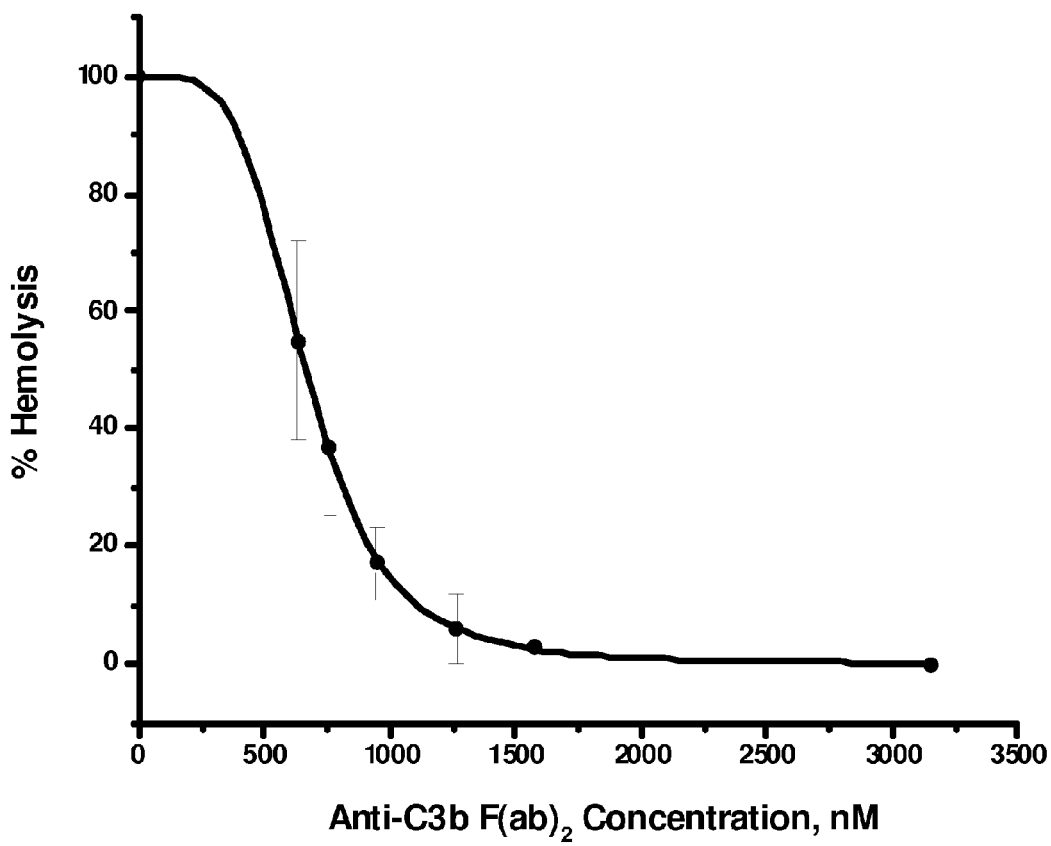
FIG. 16 illustrates that the that anti-C3b binding to C3b is has an stoichiometric relationship of 1 to 3.2

FIG. 14 shows that two of the clones bind substrate-bound C3b.

Example 10

Chimeric Anti-C3b Monoclonal Antibodies Inhibit Alternative Complement Pathway Chimeric anti-C3b antibody Fab binds C3b and inhibit alternative pathway dependent lysis of erythrocytes. The assay is the same as described in Example 3.

Example 11

Anti-C3b Monoclonal Antibody Neutralizes C3b with a Ratio of 0.33 to 1 (Antibody to C3b)

Anti-C3b antibody at various concentrations was added to a fixed concentration of normal human serum. The serum-antibody mix was added to rabbit erythrocytes and subjected to hemolysis assay as shown in Example 3. The antibody inhibited erythrocyte hemolysis at higher concentration with an inflexion point at nearly 1000 nM concentration of the antibody. The total C3 present is in the range of 3200 nM. These data suggest a stoichiometric ratio of antibody to C3 being 0.33 to 1.

Example 12

CDR Grafting of the Muring CDRs into Human Framework Regions

Murine CDRs were grafted into various frameworks to generate humanized antibodies shown in FIGS. 17 and 18. Both frameworks and CDRs are included in FIG. 19 and frameworks are included in FIGS. 20, 21, and 22.

Having described the invention, we claim:

1. An isolated anti-C3b antibody or portion thereof comprising a heavy chain variable domain including 3 CDRs having amino acid sequences of SEQ ID NO: 12, SEQ ID NO: 14, and SEQ ID NO: 16 and a light chain variable domain including 3CDRs having amino acid sequences of SEQ ID NO: 19, SEQ ID NO: 21, and SEQ ID NO: 23.

2. The anti-C3b antibody or portion thereof of claim 1, comprising humanized frame work regions, wherein the humanized framework regions are selected from humanized framework regions SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

3. The anti-C3b antibody or portion thereof of claim 1, comprising humanized or non-natural framework regions, wherein the humanized or non-natural framework regions are selected from SEQ ID NO: 11, SEQ ID NO: 13, SEQ ID NO: 15, SEQ ID NO: 17, SEQ ID NO: 18, SEQ ID NO: 20, SEQ ID NO: 22, and SEQ ID NO: 24.

4. The anti-C3b antibody or portion thereof of claim 1, comprising humanized or non-natural framework regions, wherein the humanized or non-natural framework regions are selected from SEQ ID NO: 25, SEQ ID NO: 26, SEQ ID NO: 27, SEQ ID NO: 28, SEQ ID NO: 29, SEQ ID NO: 30, SEQ ID NO: 31, and SEQ ID NO: 32.

5. The anti-C3b antibody or portion thereof of claim 1, comprising humanized or non-natural framework regions, wherein the humanized or non-natural framework regions are selected from SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48.

6. The anti-C3b antibody or portion thereof of claim 1, wherein the antibody or portion thereof inhibits the formation of newly produced PC3bBb.

7. The anti-C3b antibody or portion thereof of claim 1, wherein the antibody or antigen binding portion thereof inhibits the formation of newly produced C3a, C5a, SC5b-9.

8. The anti-C3b antibody or portion thereof of claim 1, wherein the antibody or portion thereof inhibits the activation of neutrophil, monocytes, and platelets.

9. The anti-C3b antibody or portion thereof of claim 1, wherein the antibody or portion thereof, inhibits the lysis of erythrocytes.

10. A pharmaceutical composition comprising a therapeutically effective amount of an anti-C3b antibody or portion thereof of claim 1.

11. A method of treating a disorder wherein complement activation contributes to the disorder pathology in a subject in need thereof, comprising: administering a therapeutically effective amount of an anti-C3b antibody or portion thereof that includes a heavy chain variable domain including 3 CDRs having amino acid sequences of SEQ ID NO: 12, SEQ ID NO: 14, and SEQ ID NO: 16 and a light chain variable domain including 3CDRs having amino acid sequences of SEQ ID NO: 19, SEQ ID NO: 21, and SEQ ID NO: 23.

12. The method of claim 11, wherein the disorder is an inflammatory disorder or an autoimmune disease.

13. The method of claim 11, wherein the disorder is an ocular disorder.

14. The method of claim 13, wherein the ocular disorder is selected from the group consisting of wet and dry age related macular degeneration, choroidal neovascularization, uveitis, diabetic retinopathy, diabetic macular edema, pathological myopia, Von Hippel-Lindau disease, diabetic retinopathy, histoplasmosis of the eye, diabetic retinopathy, choroidal neovascularization (CNV), Central Retinal Vein Occlusion (CRVO), corneal neovascularization, geographic atrophy, drusen disease, and retinal neovascularization.

15. The method of claim 11, wherein the disorder is selected from the group consisting of asthma, chronic obstructive pulmonary disease ("COPD"), allergic bronchopulmonary aspergillosis, hypersensitivity pneumonia, eosinophilic pneumonia, emphysema, bronchitis, allergic bronchitis bronchiecstasis, cyctic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, parasitic lung disease, respiratory syncytial virus ("RSV") infection, parainfluenza virus ("PIV") infection, rhinovirus ("RV") infection, and adenovirus infection.

* * * * *

```
                        SEQUENCE LISTING

<160> NUMBER OF SEQ ID NOS: 48

<210> SEQ ID NO 1
<211> LENGTH: 120
<212> TYPE: PRT
<213> ORGANISM: Mus musculus

<400> SEQUENCE: 1

Gln Val Gln Leu Gln Gln Ser Gly Ala Glu Ile Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asp Ile Tyr Pro Val Arg Gly Ile Thr Asn Tyr Ser Glu Lys Phe
    50                  55                  60

Lys Asn Lys Ala Lys Met Ile Pro Asp Thr Ser Ser Ser Thr Val Tyr
65                  70                  75                  80

Met Gln Leu Ser Ser Leu Thr Ser Glu Asp Ser Ala Val Tyr Tyr Cys
                85                  90                  95

Ser Arg Gly Asn Phe Gly Asn Phe Asp Ala Met Asp Tyr Trp Gly Gln
            100                 105                 110

Gly Thr Ser Val Thr Val Ser Ser
        115                 120

<210> SEQ ID NO 2
<211> LENGTH: 110
<212> TYPE: PRT
<213> ORGANISM: Mus musculus

<400> SEQUENCE: 2

Gln Ile Val Leu Thr Gln Ser Pro Ala Ile Leu Ser Ala Ser Pro Gly
1               5                   10                  15

Glu Lys Val Thr Met Thr Cys Ser Ala Thr Ser Ser Ile Thr Tyr Ile
            20                  25                  30

His Trp Tyr Gln Gln Lys Ser Gly Thr Ser Pro Lys Arg Trp Ile Tyr
        35                  40                  45

Asp Thr Ser Arg Leu Ala Ser Gly Val Pro Thr Arg Phe Ser Gly Ser
    50                  55                  60
```

```
Gly Ser Gly Thr Ser Tyr Ser Leu Thr Ile Ser Thr Met Glu Ala Glu
 65                  70                  75                  80

Asp Ala Ala Thr Tyr Tyr Cys Gln Gln Trp Ser Ser Asn Pro Pro Thr
                 85                  90                  95

Phe Gly Gly Gly Thr Lys Leu Glu Ile Lys Arg Thr Val Ala
            100                 105                 110

<210> SEQ ID NO 3
<211> LENGTH: 120
<212> TYPE: PRT
<213> ORGANISM: Homo sapiens

<400> SEQUENCE: 3

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Thr Ser Tyr
                 20                  25                  30

Trp Ile Asn Trp Ile Arg Gln Ser Pro Ser Arg Gly Leu Glu Trp Leu
             35                  40                  45

Gly Asp Ile Tyr Pro Val Arg Gly Ile Thr Asn Tyr Ser Glu Lys Phe
         50                  55                  60

Lys Asn Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Asn Phe Gly Asn Phe Asp Ala Met Asp Tyr Trp Gly Gln
            100                 105                 110

Gly Thr Leu Val Thr Val Ser Ser
            115                 120

<210> SEQ ID NO 4
<211> LENGTH: 110
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
 1               5                  10                  15

Asp Arg Val Thr Ile Thr Cys Ser Ala Thr Ser Ser Ile Thr Tyr Ile
                 20                  25                  30

His Trp Tyr Gln Gln Lys Pro Gly Lys Ala Pro Lys Leu Leu Ile Tyr
             35                  40                  45

Asp Thr Ser Arg Leu Ala Ser Gly Val Pro Ser Arg Phe Ser Gly Ser
         50                  55                  60

Gly Ser Gly Thr Glu Phe Thr Leu Thr Ile Ser Ser Leu Gln Ser Glu
 65                  70                  75                  80

Asp Phe Ala Val Tyr Tyr Cys Gln Gln Trp Ser Ser Asn Pro Pro Thr
                 85                  90                  95

Phe Gly Gln Gly Thr Lys Val Glu Ile Lys Arg Thr Val Ala
            100                 105                 110

<210> SEQ ID NO 5
<211> LENGTH: 120
<212> TYPE: PRT
<213> ORGANISM: Homo sapiens
```

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Tyr Thr Phe Thr Ser Tyr
                20                  25                  30

Trp Ile Asn Trp Val Arg Gln Ala Pro Gly Lys Gly Leu Glu Trp Val
            35                  40                  45

Ser Asp Ile Tyr Pro Val Arg Gly Ile Thr Asn Tyr Ser Glu Lys Phe
        50                  55                  60

Lys Asn Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Asn Phe Gly Asn Phe Asp Ala Met Asp Tyr Trp Gly Gln
            100                 105                 110

Gly Thr Leu Val Thr Val Ser Ser
        115                 120

<210> SEQ ID NO 6
<211> LENGTH: 110
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Thr Tyr Ile
                20                  25                  30

His Trp Tyr Gln Gln Lys Pro Gly Lys Ala Pro Lys Leu Leu Ile Tyr
            35                  40                  45

Asp Thr Ser Arg Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Val Ala Thr Tyr Tyr Cys Gln Gln Trp Ser Asn Pro Pro Thr
                85                  90                  95

Phe Gly Gln Gly Thr Lys Val Glu Ile Lys Arg Thr Val Ala
            100                 105                 110

<210> SEQ ID NO 7
<211> LENGTH: 120
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
                20                  25                  30

Trp Ile Asn Trp Val Arg Gln Ala Pro Gly Lys Gly Leu Glu Trp Val
            35                  40                  45

Gly Asp Ile Tyr Pro Val Arg Gly Ile Thr Asn Tyr Ser Glu Lys Phe
        50                  55                  60

Lys Asn Arg Phe Thr Phe Ser Leu Asp Thr Ser Lys Ser Thr Ala Tyr
65                  70                  75                  80

-continued

Leu Gln Met Asn Ser Leu Arg Ala Glu Asp Thr Ala Val Tyr Tyr Cys
                    85                  90                  95

Ala Lys Gly Asn Phe Gly Asn Phe Asp Ala Met Asp Tyr Trp Gly Gln
            100                 105                 110

Gly Thr Leu Val Thr Val Ser Ser
        115                 120

<210> SEQ ID NO 8
<211> LENGTH: 110
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Thr Tyr Ile
            20                  25                  30

His Trp Tyr Gln Gln Lys Pro Gly Lys Ala Pro Lys Val Leu Ile Tyr
        35                  40                  45

Asp Thr Ser Arg Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Val Glu Ile Lys Arg Thr Val Ala
            100                 105                 110

<210> SEQ ID NO 9
<211> LENGTH: 120
<212> TYPE: PRT
<213> ORGANISM: Homo sapiens

<400> SEQUENCE: 9

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Ser Tyr
            20                  25                  30

Trp Ile Asn Trp Val Arg Gln Ala Thr Gly Gln Gly Leu Glu Trp Met
        35                  40                  45

Gly Asp Ile Tyr Pro Val Arg Gly Ile Thr Asn Tyr Ser Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn Phe Gly Asn Phe Asp Ala Met Asp Tyr Trp Gly Gln
            100                 105                 110

Gly Thr Leu Val Thr Val Ser Ser
        115                 120

<210> SEQ ID NO 10
<211> LENGTH: 110
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Thr Tyr Ile
            20                  25                  30

His Trp Tyr Gln Gln Lys Pro Gly Lys Ala Pro Lys Leu Leu Ile Tyr
        35                  40                  45

Asp Thr Ser Arg Leu Ala Ser Gly Ile Pro Pro Arg Phe Ser Gly Ser
    50                  55                  60

Gly Tyr Gly Thr Glu Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Pro Thr
                85                  90                  95

Phe Gly Gln Gly Thr Lys Val Glu Ile Lys Arg Thr Val Ala
            100                 105                 110

<210> SEQ ID NO 11
<211> LENGTH: 25
<212> TYPE: PRT
<213> ORGANISM: Homo sapiens

<400> SEQUENCE: 11

Glu Val Gln Leu Val Gln Ser Gly Ala Glu Val Lys Lys Pro Gly Glu
1               5                   10                  15

Ser Leu Arg Ile Ser Cys Lys Gly Ser
            20                  25

<210> SEQ ID NO 12
<211> LENGTH: 10
<212> TYPE: PRT
<213> ORGANISM: Mus musculus

<400> SEQUENCE: 12

Gly Tyr Thr Phe Thr Ser Tyr Trp Ile Asn
1               5                   10

<210> SEQ ID NO 13
<211> LENGTH: 14
<212> TYPE: PRT
<213> ORGANISM: Homo sapiens

<400> SEQUENCE: 13

Trp Ile Arg Gln Ser Pro Ser Arg Gly Leu Glu Trp Leu Gly
1               5                   10

<210> SEQ ID NO 14
<211> LENGTH: 17
<212> TYPE: PRT
<213> ORGANISM: Mus musculus

<400> SEQUENCE: 14

Asp Ile Tyr Pro Val Arg Gly Ile Thr Asn Tyr Ser Glu Lys Phe Lys
1               5                   10                  15

Asn

<210> SEQ ID NO 15
<211> LENGTH: 32
<212> TYPE: PRT
<213> ORGANISM: Homo sapiens

```
<400> SEQUENCE: 15

Arg Val Thr Ile Ser Ala Asp Lys Ser Ile Ser Thr Ala Tyr Leu Gln
 1               5                  10                  15

Trp Ser Ser Leu Lys Ala Ser Asp Thr Ala Met Tyr Tyr Cys Ala Arg
                20                  25                  30

<210> SEQ ID NO 16
<211> LENGTH: 11
<212> TYPE: PRT
<213> ORGANISM: Mus musculus

<400> SEQUENCE: 16

Gly Asn Phe Gly Asn Phe Asp Ala Met Asp Tyr
 1               5                  10

<210> SEQ ID NO 17
<211> LENGTH: 11
<212> TYPE: PRT
<213> ORGANISM: Homo sapiens

<400> SEQUENCE: 17

Trp Gly Gln Gly Thr Leu Val Thr Val Ser Ser
 1               5                  10

<210> SEQ ID NO 18
<211> LENGTH: 23
<212> TYPE: PRT
<213> ORGANISM: Homo sapiens

<400> SEQUENCE: 18

Asp Ile Gln Met Thr Gln Ser Pro Ser Ser Leu Ser Ala Ser Val Gly
 1               5                  10                  15

Asp Arg Val Thr Ile Thr Cys
                20

<210> SEQ ID NO 19
<211> LENGTH: 10
<212> TYPE: PRT
<213> ORGANISM: Mus musculus

<400> SEQUENCE: 19

Ser Ala Thr Ser Ser Ile Thr Tyr Ile His
 1               5                  10

<210> SEQ ID NO 20
<211> LENGTH: 15
<212> TYPE: PRT
<213> ORGANISM: Homo sapiens

<400> SEQUENCE: 20

Trp Tyr Gln Gln Lys Pro Gly Lys Ala Pro Lys Leu Leu Ile Tyr
 1               5                  10                  15

<210> SEQ ID NO 21
<211> LENGTH: 7
<212> TYPE: PRT
<213> ORGANISM: Mus musculus

<400> SEQUENCE: 21

Asp Thr Ser Arg Leu Ala Ser
 1               5
```

```
<210> SEQ ID NO 22
<211> LENGTH: 32
<212> TYPE: PRT
<213> ORGANISM: Homo sapiens

<400> SEQUENCE: 22

Gly Val Pro Ser Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 23
<211> LENGTH: 9
<212> TYPE: PRT
<213> ORGANISM: Mus musculus

<400> SEQUENCE: 23

Gln Gln Trp Ser Ser Asn Pro Pro Thr
1               5

<210> SEQ ID NO 24
<211> LENGTH: 14
<212> TYPE: PRT
<213> ORGANISM: Homo sapiens

<400> SEQUENCE: 24

Phe Gly Gln Gly Thr Lys Val Glu Ile Lys Arg Thr Val Ala
1               5                   10

<210> SEQ ID NO 25
<211> LENGTH: 25
<212> TYPE: PRT
<213> ORGANISM: Homo sapiens

<400> SEQUENCE: 25

Glu Val Gln Leu Val Glu Ser Gly Gly Leu Val Gln Pro Gly Arg
1               5                   10                  15

Ser Leu Arg Leu Ser Cys Ala Ala Ser
            20                  25

<210> SEQ ID NO 26
<211> LENGTH: 14
<212> TYPE: PRT
<213> ORGANISM: Homo sapiens

<400> SEQUENCE: 26

Trp Val Arg Gln Ala Pro Gly Lys Gly Leu Glu Trp Val Ser
1               5                   10

<210> SEQ ID NO 27
<211> LENGTH: 32
<212> TYPE: PRT
<213> ORGANISM: Homo sapiens

<400> SEQUENCE: 27

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 28
<211> LENGTH: 11
<212> TYPE: PRT
<213> ORGANISM: Homo sapiens
```

```
<400> SEQUENCE: 28

Trp Gly Gln Gly Thr Leu Val Thr Val Ser Ser
1               5                   10

<210> SEQ ID NO 29
<211> LENGTH: 23
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 30
<211> LENGTH: 15
<212> TYPE: PRT
<213> ORGANISM: Homo sapiens

<400> SEQUENCE: 30

Trp Tyr Gln Gln Lys Pro Gly Lys Ala Pro Lys Leu Leu Ile Tyr
1               5                   10                  15

<210> SEQ ID NO 31
<211> LENGTH: 32
<212> TYPE: PRT
<213> ORGANISM: Homo sapiens

<400> SEQUENCE: 31

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 32
<211> LENGTH: 14
<212> TYPE: PRT
<213> ORGANISM: Homo sapiens

<400> SEQUENCE: 32

Phe Gly Gln Gly Thr Lys Val Glu Ile Lys Arg Thr Val Ala
1               5                   10

<210> SEQ ID NO 33
<211> LENGTH: 25
<212> TYPE: PRT
<213> ORGANISM: Homo sapiens

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 34
<211> LENGTH: 14
<212> TYPE: PRT
<213> ORGANISM: Homo sapiens

<400> SEQUENCE: 34

Trp Val Arg Gln Ala Pro Gly Lys Gly Leu Glu Trp Val Gly
1               5                   10
```

<210> SEQ ID NO 35
<211> LENGTH: 32
<212> TYPE: PRT
<213> ORGANISM: Homo sapiens

<400> SEQUENCE: 35

Arg Phe Thr Phe Ser Leu Asp Thr Ser Lys Ser Thr Ala Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 36
<211> LENGTH: 11
<212> TYPE: PRT
<213> ORGANISM: Homo sapiens

<400> SEQUENCE: 36

Trp Gly Gln Gly Thr Leu Val Thr Val Ser Ser
1               5                   10

<210> SEQ ID NO 37
<211> LENGTH: 23
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 38
<211> LENGTH: 15
<212> TYPE: PRT
<213> ORGANISM: Homo sapiens

<400> SEQUENCE: 38

Trp Tyr Gln Gln Lys Pro Gly Lys Ala Pro Lys Val Leu Ile Tyr
1               5                   10                  15

<210> SEQ ID NO 39
<211> LENGTH: 32
<212> TYPE: PRT
<213> ORGANISM: Homo sapiens

<400> SEQUENCE: 39

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 40
<211> LENGTH: 14
<212> TYPE: PRT
<213> ORGANISM: Homo sapiens

<400> SEQUENCE: 40

Phe Gly Gln Gly Thr Lys Val Glu Ile Lys Arg Thr Val Ala
1               5                   10

<210> SEQ ID NO 41
<211> LENGTH: 25
<212> TYPE: PRT
<213> ORGANISM: Homo sapiens -continued

```
<400> SEQUENCE: 41

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 42
<211> LENGTH: 14
<212> TYPE: PRT
<213> ORGANISM: Homo sapiens

<400> SEQUENCE: 42

Trp Val Arg Gln Ala Thr Gly Gln Gly Leu Glu Trp Met Gly
1               5                   10

<210> SEQ ID NO 43
<211> LENGTH: 32
<212> TYPE: PRT
<213> ORGANISM: Homo sapiens

<400> SEQUENCE: 43

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 44
<211> LENGTH: 11
<212> TYPE: PRT
<213> ORGANISM: Homo sapiens

<400> SEQUENCE: 44

Trp Gly Gln Gly Thr Leu Val Thr Val Ser Ser
1               5                   10

<210> SEQ ID NO 45
<211> LENGTH: 23
<212> TYPE: PRT
<213> ORGANISM: Homo sapiens

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 46
<211> LENGTH: 15
<212> TYPE: PRT
<213> ORGANISM: Homo sapiens

<400> SEQUENCE: 46

Trp Tyr Gln Gln Lys Pro Gly Lys Ala Pro Lys Leu Leu Ile Tyr
1               5                   10                  15

<210> SEQ ID NO 47
<211> LENGTH: 32
<212> TYPE: PRT
<213> ORGANISM: Homo sapiens
```

-continued

```
<400> SEQUENCE: 47

Gly Ile Pro Pro Arg Phe Ser Gly Ser Gly Tyr Gly Thr Glu Phe Thr
1               5                   10                  15

Phe Thr Ile Ser Ser Leu Glu Ala Glu Asp Ala Ala Thr Tyr Tyr Cys
                20                  25                  30

<210> SEQ ID NO 48
<211> LENGTH: 14
<212> TYPE: PRT
<213> ORGANISM: Homo sapiens

<400> SEQUENCE: 48

Phe Gly Gln Gly Thr Lys Val Glu Ile Lys Arg Thr Val Ala
1               5                   10
```